US012791486B2

(12) United States Patent
You et al.

(10) Patent No.: US 12,791,486 B2
(45) Date of Patent: Nov. 10, 2026

(54) SURFACE-ENHANCED RAMAN SCATTERING SENSING PLATFORM AND DETECTION METHOD OF SUBSTANCE TO BE DETECTED USING THE SAME

(71) Applicant: KOREA RESEARCH INSTITUTE OF STANDARDS AND SCIENCE, Daejeon (KR)

(72) Inventors: Eun-Ah You, Daejeon (KR); Jae-Eul Shim, Gimhae-si (KR); Young Jun Kim, Seoul (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 560 days.

(21) Appl. No.: 18/317,677

(22) Filed: May 15, 2023

(65) Prior Publication Data

US 2023/0366824 A1 Nov. 16, 2023

(30) Foreign Application Priority Data

May 16, 2022 (KR) ........................ 10-2022-0059551
Nov. 7, 2022 (KR) ........................ 10-2022-0146690

(51) Int. Cl.
*G01N 21/65* (2006.01)
*G01N 33/543* (2006.01)
(Continued)

(52) U.S. Cl.
CPC ......... *G01N 21/658* (2013.01); *G01N 33/543* (2013.01); *G01N 33/563* (2013.01);
(Continued)

(58) Field of Classification Search
CPC .. G01N 21/658; G01N 33/543; G01N 33/563; G01N 33/56983; G01N 2021/656; G01N 2469/20; G01N 33/54373
See application file for complete search history.

(56) References Cited

FOREIGN PATENT DOCUMENTS

| | | |
|---|---|---|
| KR | 20110039688 A | 4/2011 |
| KR | 20140030216 A | 3/2014 |

(Continued)

OTHER PUBLICATIONS

You'21 translation (Year: 2021).*

(Continued)

*Primary Examiner* — Kara E. Geisel
(74) *Attorney, Agent, or Firm* — Knobbe, Martens, Olson & Bear, LLP

(57) ABSTRACT

Provided is a digital surface-enhanced Raman scattering (SERS) sensing platform which allows quantitative detection of a substance to be detected reliably and reproducibly with an excellent limit of detection in a large dynamic range, including: a surface-enhanced Raman scattering (SERS) active reagent which includes Raman active particles including a spherical plasmonic metal core, a plasmonic metal shell having a surface unevenness, and a self-assembled monolayer including a Raman reporter positioned between the core and the shell; a Raman spectroscopic detection unit which performs Raman mapping based on a Raman spectrum which is detected by irradiating the active reagent with an excitation light; and a digital signal analysis unit which analyzes a quantitative detection signal of a substance to be detected by a combination of a Raman signal intensity calculated from the Raman spectrum and a digital count calculated from the Raman mapping.

12 Claims, 14 Drawing Sheets

(51) Int. Cl.
*G01N 33/563* (2006.01)
*G01N 33/569* (2006.01)

(52) U.S. Cl.
CPC . *G01N 33/56983* (2013.01); *G01N 2021/656* (2013.01); *G01N 2469/20* (2013.01)

(56) References Cited

FOREIGN PATENT DOCUMENTS

| | | | | |
|---|---|---|---|---|
| KR | 101793008 | B1 | 11/2017 | |
| KR | 101841369 | B1 | 3/2018 | |
| KR | 20200040111 | A | 4/2020 | |
| KR | 20210028984 | A | 3/2021 | |
| KR | 20210028988 | A | 3/2021 | |
| KR | 102365091 | B1 | 2/2022 | |
| WO | WO-2014144133 | A1 * | 9/2014 | ......... B29C 37/0003 |
| WO | WO-2021045288 | A1 * | 3/2021 | ........... G01N 21/658 |
| WO | WO 2022/197463 | A2 | 9/2022 | |

OTHER PUBLICATIONS

Zhang et al., "Ultrasensitive detection of SARS-CoV-2 spike protein in untreated saliva using SERS-based biosensor". Biosensors and Bioelectronics 190 (Jun. 2021) 113421, in 8 pages.
Nam et al., "A digital SES sensing platform using 3D nanolaminate plasmonic crystals coupled with Au nanoparticles for accurate quantitative detection of dopamine". Nanoscale, 2021. vol. 13, No. 41, pp. 17340-17349.

* cited by examiner

Quantification

SURFACE-ENHANCED RAMAN SCATTERING SENSING PLATFORM AND DETECTION METHOD OF SUBSTANCE TO BE DETECTED USING THE SAME

CROSS-REFERENCE TO RELATED APPLICATIONS

This application claims priority under 35 U.S.C. § 119 to Korean Patent Application No. 10-2022-0059551, filed on May 16, 2022, and Korean Patent Application No. 10-2022-0146690, filed on Nov. 7, 2022, in the Korean Intellectual Property Office, the disclosure of which is incorporated herein by reference in its entirety.

TECHNICAL FIELD

The following disclosure relates to a surface-enhanced Raman scattering sensing platform and a detection method of a substance to be detected using the same, and more particularly, to a surface-enhanced Raman scattering sensing platform which allows monomolecular level detection with excellent reliability using surface-enhanced Raman scattering, and a detection method of a substance to be detected using the same.

BACKGROUND various immunoassays such as enzyme-linked immunosorbent assay (ELISA) or radioimmunoassay (RIA) are being used in order to detect biomolecules including various pathogens or various viruses contained in a biological sample for early diagnosis or treatment of diseases.

However, these immunoassays need a separate amplification process for detecting a trace substance to be desired, a time required for diagnosis is increased by the essentially involved amplification process, and inaccurate diagnosis results and diagnosis cost are increased.

In particular, detection of the antigen of the latest severe acute respiratory syndrome coronavirus 2 (SARS-CoV-2) going around should be rapidly and accurately performed for minimizing the spread of the virus, but conventional immunoassays have limitations.

Thus, a study to detect various pathogens and viruses early and rapidly by applying surface-enhanced Raman scattering (SERS) spectrometry, which uses a phenomenon in which an intensity of Raman scattering originated by surface plasmon resonance (SPR) which is collective oscillations of free electrons on the surface of a metal nanostructure increases rapidly by $10^6$ to $10^8$ times or more when molecules are adsorbed on the surface of a metal nanostructure, as a tool for ultra-sensitive chemical/biological/biochemical analysis, is being actively carried out.

However, though SERS spectrometry has high selectivity, high informativeness, and high sensitivity, signal enhancement based on Raman scattering intensity changes sensitively depending on the shape, the kind, or the like of metal nanostructure, and thus, reliability and reproducibility are deteriorated by variation in detection probability of a target substance. In particular, since a detection signal for a substance to be detected at a low concentration is not consistent, there is a limit to improving detection reliability.

In addition, there is a limit to detecting a substance to be detected at a level of 1 pM or less, and a dynamic range which is a detection section where the substance to be detected may be quantitatively measured is narrow.

Therefore, it is necessary to develop a surface-enhanced Raman scattering sensing platform which improves a limit of detection (LOD) of a substance to be detected in a large dynamic range and also has excellent reliability and reproducibility.

RELATED ART DOCUMENTS

Patent Documents

Korean Patent Laid-Open Publication No. 10-2011-0039688

SUMMARY

An embodiment of the present invention is directed to providing a surface-enhanced Raman scattering sensing platform which allows quantitative detection of a substance to be detected with excellent reliability and reproducibility, and a detection method of a substance to be detected using the same.

Another embodiment of the present invention is directed to providing a surface-enhanced Raman scattering sensing platform which may improve a limit of detection (LOD) of a substance to be detected in a large dynamic range, and a detection method of a substance to be detected using the same.

In one general aspect, a digital surface-enhanced Raman scattering (SERS) sensing platform includes: a surface-enhanced Raman scattering (SERS) active reagent which includes Raman active particles including a spherical plasmonic metal core, a plasmonic metal shell having a surface unevenness, and a self-assembled monolayer including a Raman reporter positioned between the core and the shell; a Raman spectroscopic detection unit which performs Raman mapping based on a Raman spectrum which is detected by irradiating the active reagent with an excitation light; and a digital signal analysis unit which analyzes a quantitative detection signal of a substance to be detected by a combination of a Raman signal intensity calculated from the Raman spectrum and a digital count calculated from the Raman mapping.

In the digital surface-enhanced Raman scattering (SERS) sensing platform according to an exemplary embodiment of the present invention, the digital count may be the total number of pixels of which the Raman signal intensity is more than a background threshold in a Raman map obtained by the Raman mapping.

In the digital surface-enhanced Raman scattering (SERS) sensing platform according to an exemplary embodiment of the present invention, the quantitative detection signal may be the product of the Raman signal intensity and the digital count.

In the digital surface-enhanced Raman scattering (SERS) sensing platform according to an exemplary embodiment of the present invention, the plasmonic metal shell may include plasmonic metal fine particles having an average size of 0.3D to 0.6D based on a diameter (D) of a metal core, and may have the surface unevenness by the plasmonic metal fine particles.

In the digital surface-enhanced Raman scattering (SERS) sensing platform according to an exemplary embodiment of the present invention, the self-assembled monolayer may have a thickness of 0.5 to 1.5 nm.

In the digital surface-enhanced Raman scattering (SERS) sensing platform according to an exemplary embodiment of the present invention, the Raman active particles may have a size of 100 to 150 nm.

In the digital surface-enhanced Raman scattering (SERS) sensing platform according to an exemplary embodiment of the present invention, the Raman reporter may satisfy the following Chemical Formula 1:

$NO_2$—Ar—SH (Chemical Formula 1)

wherein Ar is a (C6-C12) arylene group.

In the digital surface-enhanced Raman scattering (SERS) sensing platform according to an exemplary embodiment of the present invention, the substance to be detected may be a virus including SARS-CoV-2 and variants thereof.

In the digital surface-enhanced Raman scattering (SERS) sensing platform according to an exemplary embodiment of the present invention, the excitation light may be a near-infrared ray in a wavelength band of 750 to 800 nm.

In the digital surface-enhanced Raman scattering (SERS) sensing platform according to an exemplary embodiment of the present invention, a relative standard deviation (% RSD) of a quantitative detection signal for the substance to be detected at an extremely low concentration in a range of 1 fM to 80 fM may be 20% or less, the relative standard deviation of the quantitative detection signal for the substance to be detected being an indicator showing sensing reliability of the substance to be detected using the digital SERS sensing platform.

In another general aspect, a detection method of a substance to be detected in a sample is provided.

The detection method of a substance to be detected in a sample includes: a) preparing a Raman probe in which a first receptor (detection antibody) which may specifically bind to a substance to be detected is positioned on a surface of a Raman active particle including a spherical plasmonic metal core, a plasmonic metal shell having surface unevenness, and a self-assembled monolayer including a Raman reporter positioned between the core and the shell; b) preparing a substrate having a second receptor (capture antibody) which may specifically bind to the substance to be detected on the surface; c) forming an analysis structure by bringing a sample including the substance to be detected into contact with the substrate of step b) to capture the substance, and then further bringing the sample into contact with the Raman probe of step a) to cap the substance; d) detecting Raman spectroscopy by performing Raman mapping based on a Raman spectrum detected by irradiating the analysis structure with an excitation light; and e) obtaining a digital signal which may be quantitatively detected by a combination of a Raman signal intensity calculated from the Raman spectrum and a digital count calculated from the Raman mapping.

In the detection method according to an exemplary embodiment of the present invention, the digital count of step e) may be the total number of pixels of which the Raman signal intensity is more than a background threshold in a Raman map obtained by the Raman mapping performed in a predetermined area.

In the detection method according to an exemplary embodiment of the present invention, the digital signal may be the product of the Raman signal intensity and the digital count.

In the detection method according to an exemplary embodiment of the present invention, the excitation light irradiated in step d) may be a near-infrared ray in a wavelength band of 750 to 800 nm.

In the detection method according to an exemplary embodiment of the present invention, a relative standard deviation (% RSD) of a digital signal for the substance to be detected at an extremely low concentration in a range of 1 fM to 80 fM may be 20% or less, the relative standard deviation of the obtained digital signal being an indicator showing detection reliability of the substance to be detected.

In the detection method according to an exemplary embodiment of the present invention, a limit of detection (LOD) of the substance to be detected by the detection method may be 1 fM or less.

Other features and aspects will be apparent from the following detailed description, the drawings, and the claims.

DETAILED DESCRIPTION OF EMBODIMENTS

Figure 1A:
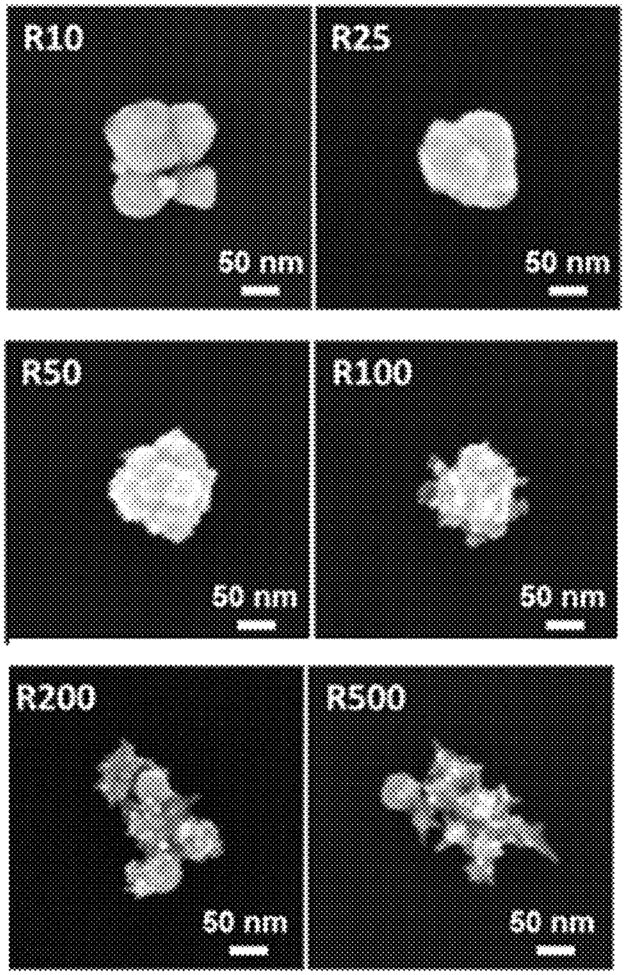
FIG. 1A is a drawing illustrating a scanning electron microscopic (SEM) image of Raman active particles prepared according to Examples 1 to 6.

Hereinafter, the surface-enhanced Raman scattering sensing platform and a detection method of a substance to be detected using the same will be described in detail, with reference to the attached drawings.

The drawings to be provided below are provided by way of example so that the spirit of the present invention can be sufficiently transferred to a person skilled in the art to which the present invention pertains. Therefore, the present invention is not limited to the drawings provided below but may be embodied in many different forms, and the drawings suggested below may be exaggerated in order to clear the spirit of the present invention.

Technical terms and scientific terms used herein have the general meaning understood by those skilled in the art to which the present invention pertains, unless otherwise defined, and the description for the known function and configuration which may unnecessarily obscure the gist of the present invention will be omitted in the following description and the accompanying drawings.

In addition, the singular form used in the specification and claims appended thereto may be intended to include a plural form also, unless otherwise indicated in the context.

In the present specification and the appended claims, the terms such as “first” and “second” are not used in a limited meaning but are used for the purpose of distinguishing one constituent element from other constituent elements.

In the present specification and the appended claims, the terms such “comprise” or “have” mean that there is a characteristic or a constituent element described in the specification, and as long as it is not particularly limited, a possibility of adding one or more other characteristics or constituent elements is not excluded in advance.

Units used in the present specification and attached claims thereto without particular mention are based on weights, and as an example, a unit of % or ratio refers to a wt % or a weight ratio.

In the present specification and the appended claims, when a portion such as a membrane (layer), a region, and a constituent element is present on another portion, not only a case in which the portion is in contact with and directly on another portion but also a case in which other membranes (layers), other regions, other constitutional elements are interposed between the portions is included.

The digital surface-enhanced Raman scattering (SERS) sensing platform according to the present invention includes: a surface-enhanced Raman scattering (SERS) active reagent which includes Raman active particles including a spherical plasmonic metal core, a plasmonic metal shell having a surface unevenness, and a self-assembled monolayer including a Raman reporter positioned between the core and the shell; a Raman spectroscopic detection unit which performs Raman mapping based on a Raman spectrum which is detected by irradiating the active reagent with an excitation light; and a digital signal analysis unit which analyzes a quantitative detection signal of a substance to be detected by a combination of a Raman signal intensity calculated from the Raman spectrum and a digital count calculated from the Raman mapping.

In the detection of the target substance to be detected, the conventional detection based on SERS spectrometry generally quantitatively detected a substance to be detected with a Raman intensity sensed in a specific Raman shift as a detection signal, but signal enhancement based on a Raman intensity sensitively changes depending on the shape, the kind, or the like of Raman active particles, and thus, the detection probability of the target substance to be detected is not consistent, and there is a limit to improve reliability and reproducibility.

However, the SERS sensing platform according to the present invention uses a surface-enhanced Raman scattering (SERS) active reagent including Raman active particles including a spherical plasmonic metal core, a plasmonic metal shell having surface unevenness, and a self-assembled monolayer including a Raman reporter positioned between the core and the shell, thereby decreasing volatility of detection probability by the Raman active particles, and unlike before, since the quantitative detection signal of the substance to be detected is analyzed by a combination of a Raman signal intensity and a digital count, the substance to be detected may be accurately quantitatively detected in a large dynamic range, and also, a limit of detection to detect a substance to be detected at an extremely low concentration may be also improved.

Furthermore, the reliability and the reproducibility for the quantitative detection of the substance to be detected may be significantly improved by the quantitative detection signal by a combination of a Raman signal intensity and a digital count together with the Raman active particles included in the active reagent.

In an exemplary embodiment, the Raman active particle may include: a spherical plasmonic metal core; a plasmonic metal shell having surface unevenness; and a self-assembled monolayer including a Raman reporter which binds to each of the core and the shell and is positioned between the core and the shell.

As a specific example, the Raman reporter may satisfy the following Chemical Formula 1:

$NO_2$—Ar—SH (Chemical Formula 1)

wherein Ar is a (C6-C12) arylene group.

Specifically, the Raman active particles described above have a core-shell structure, and include a self-assembled monolayer including a Raman reporter which is positioned between a core and a shell and is represented by a chemical formula of $NO_2$—Ar—SH (Ar is a (C6-C12) arylene group) having a sulfhydryl group (—HS) and a nitro group (—$NO_2$) which are surface bonding functional groups at both ends, thereby forming a nanogap corresponding to the thickness of the self-assembled monolayer having a strictly adjusted thickness due to the characteristic of self assembling in the Raman active particles.

In addition, since the shape of the plasmonic metal core is spherical, the self-assembled monolayer has a spherical shape, and in the case of the plasmonic metal shell also, the inner shape of the metal shell in contact with the self-assembled monolayer may have a spherical shape. Thus, the nanogap is positioned in the entire area of the Raman active particle, and the nanogap having a uniform size may be positioned in all directions based on the radical direction.

In particular, since the self-assembled monolayer positioned between the core and shell includes the Raman reporter satisfying Chemical Formula 1, the Raman reporter is positioned at positions which are well-defined and radically identical in the Raman active particle, and the Raman reporter which is uniformly positioned at a high density in the entire area of the Raman active particle is positioned at the nanogap, that is, a hot spot where surface plasmon resonance occurs locally. That is to say, the Raman active particle may have a SERS hot spot area which are uniformly present in the entire area of the Raman active particle by an SERS effect which is caused by the Raman reporter satisfying Chemical Formula 1 positioned in the hot spot.

In addition, the Raman reporter satisfying Chemical Formula 1 allows formation of unevenness having a uniform size in the entire area of the surface of the metal shell, whereby the Raman active particles may have isotropic Raman activity, the Raman active particle as such may show uniform SERS activity based on the particles, there is little deviation of Raman activity between particles so that uniform SERS activity between particles may be shown, and furthermore, since the surface of the metal shell has an uneven structure, a strong electromagnetic field is formed to significantly improve Raman intensity, and thus, a Raman signal intensity may be better and a higher correlation may be shown than before.

Here, the correlation may refer to a relation with the number of Raman active particles in which a SERS signal is detected, among all Raman active particles in Raman mapping. That is, when a SERS signal is detected in many Raman active particles, based on the total number of Raman active particles, it is said that the correlation is high.

As an exemplary embodiment, the plasmonic metal shell includes plasmonic metal fine particles having an average size of 0.1 to 1.2D, specifically 0.2 to 1.0D, and more specifically 0.3 to 0.6 D, based on the diameter (D) of a metal core, and may have surface unevenness by the plasmonic metal fine particles.

Specifically, since in the plasmonic metal shell, the uneven structure due to the metal fine particles may have a uniform size by the Raman reporter satisfying Chemical Formula 1 and the metal shell formed of the metal fine particles having the average size in the range described above, as described above, hot spots on the surface of the shell itself, that is, hot spots according to a spaced distance between closest concave and convex having a uniform size, may be formed, together with hot spots by the nanogap between the metal core and the metal shell, and thus, it is more advantageous for Raman signal enhancement.

Here, the metal core may have an average diameter of 20 to 100 nm, specifically 20 to 80 nm, more specifically 30 to 70 nm, and still more specifically 40 to 60 nm.

Since the average diameter of the metal core satisfies the range, the metal core has an appropriate radius of curvature to form a dense self-assembled monolayer, and thus, nanogaps having a uniform size may be present by the self-assembled monolayer by an interaction between the metal core and the Raman reporter.

As an exemplary embodiment, the Raman active particles having a core-shell structure may have an average size of 100 to 250 nm, specifically 100 to 200 nm, more specifically 100 to 150 nm, and still more specifically 120 to 130 nm.

As a specific example, in the core-shell structure, the shell may have a thickness of 15 to 60 nm, preferably 20 to 50 nm, and more preferably 25 to 40 nm.

Here, the thickness of the shell may refer to a distance from the surface of the core to the outermost part of the shell.

As described above, since the metal shell which is formed of metal fine particles having the average size described above based on the diameter of the metal core has the thickness described above and has the surface uneven structure, the Raman active particles of the core-shell structure form a strong electromagnetic field to significantly improve a Raman intensity.

In addition, since in the metal shell, the metal fine particles themselves protrude to form bumpy unevenness in the entire area of the surface of the metal shell, the sensitivity of the Raman active particles may be increased by the metal shell, uniform Raman activity may be shown in one particle, and also, uniformity of Raman activity between particles may not be impaired.

As a specific example, each of the plasmonic metal core and the plasmonic metal shell may be a metal generating surface plasmon by an interaction with light. As an example, each of the plasmon metal core and the plasmon metal shell may be gold, silver, platinum, palladium, nickel, aluminum, copper, a mixture thereof, an alloy thereof, or the like. However, each of the plasmonic metal core and the plasmonic metal shell may be gold or silver, considering biocompatibility.

As another specific example, the plasmonic metal core and the plasmonic metal shell may be the same metal, and as an example, the plasmonic metal core and the plasmonic metal shell may be gold.

In an exemplary embodiment, the self-assembled monolayer positioned between the plasmonic metal core and the plasmonic metal shell may be a self-assembled monolayer of the Raman reporter, and the Raman reporter may refer to an organic compound (organic molecule) including a Raman active molecule, or an organic compound (organic molecule) having a binding force to the metal of the metal core and including a Raman active molecule.

As a specific example, the Raman reporter may be a Raman active molecule in a benzene ring form, and the Raman active molecule in a benzene ring form may be one or more selected from 2-nitrobenzenethiol (2-NBT) and 4-nitrobenzenethiol (4-NBT), and preferably 4-nitrobenzenethiol (4-NBT).

As a specific example, the Raman reporter may satisfy the following Chemical Formula 2:

(Chemical Formula 2)

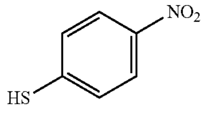

Specifically, since the Raman reporter satisfies Chemical Formula 2, the self-assembled monolayer has a spherical shape which is very similar to the radius of curvature of the spherical metal core, the size of the nanogap positioned in the entire area of the Raman active particle is uniform, and thus, the Raman signal intensity may be improved.

In particular, when the average diameter of the plasmonic metal core satisfies the range described above, the self-assembled monolayer formed by the interaction with the Raman reporter satisfying Chemical Formula 2 forms a SERS hot spot area which is uniformly present in the entire area of the Raman active particle, thereby significantly improving the Raman signal intensity.

In addition, since the nanogaps are formed between the metal core and the metal shell by the Raman reporter binding to the metal core, a length (size) of the Raman reporter may be 3 nm or less, specifically 0.5 to 1.5 nm, and more specifically 0.5 to 1 nm, in terms of forming hot spots where stronger signal enhancement is done. Here, the length (size) of the Raman reporter corresponds to the thickness of the self-assembled monolayer, of course.

Since the SERS active reagent included in the SERS sensing platform according to the present invention includes the Raman active particles described above, the substance to be detected by the Raman active particles may decrease variability in probability of detection to improve detection reliability.

Here, the SERS active reagent may include Raman active particles which further include a receptor binding to the substance to be detected.

As an example, the receptor may include any material which is known to be specifically bonded to the substance to be detected, such as complementary bonding between enzyme-substrate, antigen-antibody, protein-protein, or DNAs. Here, the receptor may include a functional group such as a thiol group, a carboxyl group, or an amine group which spontaneously binds to the metal of the metal shell included in the Raman active particle, and the receptor may be in a state of chemically binding to the metal shell by the functional group.

In addition, the Raman active particles included in the SERS active reagent may further include a blocking molecule which covers the surface area of the metal shell to which the receptor does not bind, in addition to the receptor. The blocking molecule prevents an undesired interaction between the shell surface itself, not the receptor, and the substance to be detected, and may serve to make orientation of the receptor positioned on the surface of the shell more constant. The blocking molecule may be any material which is commonly used for preventing nonspecific binding on the metal surface in the biosensor field, such as bovine serum albumin (SBA).

As an exemplary embodiment, the SERS sensing platform may include a Raman spectroscopic detection unit which performs Raman mapping based on a Raman spectrum which is detected by irradiating the active reagent described above with an excitation light.

As a specific example, the excitation light may be a near-infrared ray having a wavelength of 750 nm or more, specifically a near-infrared ray having a wavelength of 750 nm to 1500 nm, and more specifically a near-infrared ray having a wavelength of 750 nm to 1000 nm or 750 nm to 800 nm. That is, the substance to be detected may be detected and analyzed by irradiating the active reagent including the Raman active particles with an excitation light in a near-infrared band.

When a biomaterial including a biochemical material is detected by using the near-infrared ray satisfying the wavelength range described above as the excitation light, a fluorescence phenomenon may be suppressed to improve detection reliability and light stability of the Raman active particles may be improved. Herein, the light stability may mean that the Raman intensity detected by the Raman active particles after irradiating the excitation light for 30 minutes satisfies 50% or more, 55% or more, 60% or more, 65% or more compared with the initial Raman intensity.

As an exemplary embodiment, the Raman mapping which is performed by the Raman spectroscopic detection unit may be Raman mapping for a predetermined sized area, and the predetermined size may be 1 to 100 μm×1 to 100 μm, but is not limited thereto.

In addition, a mapping interval in the Raman mapping may be at a level of 0.1 μm to 10 μm to each of the axes perpendicular to each other, an output of excitation light (excitation laser light) may be at a level of 1 mW to 90 mW, and as a practical example, 1 mW to 10 mW, an excitation light irradiation time may be 0.5 to 10 seconds, and the number of scanning may be 1 to 5, but are not limited thereto.

As a specific example, the SERS sensing platform may include a digital signal analysis unit which analyzes a quantitative detection signal of a substance to be detected by a combination of a Raman signal intensity calculated from a Raman spectrum and a digital count calculated from the Raman mapping.

As a specific example, the digital count calculated from the Raman mapping may be the total number of pixels of which the Raman signal intensity is more than a background threshold in a Raman map obtained by the Raman mapping.

Specifically, the Raman mapping performed for the predetermined sized area may be divided into each pixel by mapping interval. Here, when the Raman signal intensity in each divided pixel is more than a background threshold, the total number of pixels obtained by counting is the digital count.

As an example, when the predetermined size is 10 μm×10 μm and a mapping interval is 1 μm, the Raman map is divided into a total of 100 pixels. Here, the Raman signal intensity in each pixel is counted when it is more than the background threshold, and the total number of pixels counted is the digital count.

Herein, the background threshold may be set using the sum of maximum Raman intensities obtained by Raman analysis performed for a reagent which does not include the Raman active particles and the standard deviation.

As a specific example, the background threshold may be the sum of a maximum background intensity and a background standard deviation.

That is, the value of the sum of the background standard deviations which are the standard deviations of the maximum background Raman intensity detected in the Raman mapping which is performed for an area having a size predetermined using a reagent including no Raman active particle and the Raman intensity detected in each pixel is set as the background threshold.

Since the background threshold is set as described above, the reliability of the quantitative detection signal for the substance to be detected at a low concentration may be improved.

As an exemplary embodiment, the quantitative detection signal to detect the substance to be detected may be the product of the Raman signal intensity calculated from the Raman spectrum and the digital count calculated from the Raman mapping.

Since unlike before, the quantitative detection signal for detecting the substance to be detected is analyzed by a combination of the Raman signal intensity and the digital count, that is, the product value of the Raman signal intensity and the digital count, the substance to be detected may be accurately quantitatively detected over a large dynamic range, and also, a limit of detection to detect the substance to be detected at an extremely low concentration may be improved, and the reliability and the reproducibility for the quantitative detection of the substance to be detected may be significantly improved.

As a specific example, a relative standard deviation of the quantitative detection signal for the substance to be detected at an extremely low concentration in a range of 1 fM to 80 fM, specifically 1 fM to 50 fM, more specifically 1 fM to 30 fM, and still more specifically 1 fM to 10 fM may be 25% or less, 24% or less, 23% or less, 22% or less, 21% or less, 20% or less, 19% or less, 18% or less, 17% or less, 16% or less, 15% or less, or 14.5% or less, the relative standard deviation (% RSD) of the quantitative detection signal for the substance to be detected being an indicator of a sensing reliability of the substance to be detected.

Herein, the quantitative detection signal may be a signal obtained by repeating the detection experiment for the same substance to be detected 5 times or more, 10 times or more, 20 times or more, 30 times or more, 40 times or more, or 50 times or more.

That is, the SERS sensing platform according to an exemplary embodiment of the present invention may be used to accurately quantitatively detect the substance to be detected with excellent reliability in a large dynamic range.

As a specific example, the substance to be detected may be a substance of biological or non-living origin including a virus.

Specifically, the substance to be detected may include lesion biomarkers having lesion specificity, pathogens, protein, nucleic acid, sugars, drugs, and the like. More specifically, the substance to be detected may viruses including SARS-CoV-2 and variants thereof.

The present invention provides a detection method of a substance to be detected in a sample.

The detection method of a substance to be detected in a sample of the present invention includes: a) preparing a Raman probe in which a first receptor (detection antibody) which may specifically bind to a substance to be detected is positioned on a surface of a Raman active particle including a spherical plasmonic metal core, a plasmonic metal shell having surface unevenness, and a self-assembled monolayer including a Raman reporter positioned between the core and the shell; b) preparing a substrate having a second receptor (capture antibody) which may specifically bind to the substance to be detected on the surface; c) forming an analysis structure by bringing a sample including the substance to be detected into contact with the substrate of step b) to capture the substance, and then further bringing the sample into contact with the Raman probe of step a) to cap the substance; d) detecting Raman spectroscopy by performing Raman mapping based on a Raman spectrum detected by irradiating the analysis structure with an excitation light; and e) obtaining a digital signal which allows quantitative analysis of the substance to be detected by a combination of a Raman signal intensity calculated from the Raman spectrum and a digital count calculated from the Raman mapping.

As a specific example, the Raman probe may include a-1) preparing Raman active particles; and a-2) immobilizing a first receptor which may specifically bind to the substance to be detected on the surface of the Raman active particles.

Herein, since the Raman active particles prepared are identical or similar to those described above, the detailed description thereof will be omitted.

The Raman active particles prepared in step a-1) may be prepared using the method described in Korean Patent Registration No. 10-2365091 B1 (Feb. 15, 2022).

Specifically, a self-assembled monolayer including a Raman reporter satisfying the following Chemical Formula 1 is formed on a spherical plasmonic metal core, and a reaction solution in which a buffer solution, the metal core on which the self-assembled monolayer has been formed, and a plasmonic metal precursor are mixed is used to form a plasmonic metal shell which encloses the metal core on which the self-assembled monolayer has been formed and has surface unevenness, thereby preparing the Raman active particles:

$NO_2$—Ar—SH (Chemical Formula 1)

wherein Ar is a (C6-C12) arylene group.

Specifically, the Raman reporter may satisfy the following Chemical Formula 2:

(Chemical Formula 2)

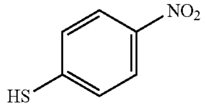

Herein, in the process of forming the plasmonic metal shell, a mole ratio between the metal precursor and the buffer included in the buffer solution may be controlled to control the size of surface unevenness and shape uniformity.

As a specific example, the mole ratio of metal precursor: buffer may be 1:5 to 250, specifically 1:10 to 150, and more specifically 1:25 to 80.

Herein, the buffer included in the buffer solution may be any one or more selected from the group consisting of 4-(2-hydroxyethyl)-1-piperazineethanesulfonic acid (HEPES), 4-(2-Hydroxyethyl)piperazine-1-ethanesulfonic acid (MES), phosphated buffered saline (PBS), tris(2-Amino-2hydroxymethyl propne-1,3-idol), phosphate buffer (PB), 3-(N-morpholino)propanesulfonic acid (MOPS), 3-[[1,3-dihydroxy-2-(hydroxymethyl)propan-2-yl]amino] propane-1-sulfonic acid (TAPS), and piperazine-N,N'-bis(2-ethanesulfonic acid) (PIPES).

The metal of the metal precursor may include gold, silver, platinum, palladium, nickel, aluminum, copper, a mixture thereof, an alloy thereof, and the like. However, the metal of the metal precursor may be preferably gold or silver, independently of the metal of the metal core, considering biostability. As an example, the metal of the metal precursor may be the same metal as the metal of the metal core, of course.

As a specific example, the metal precursor may be a gold precursor such as $HAuCl_4$, $HAuBr_4$, $NaAuCl_4$, $AuCl_3 \cdot 3H_2O$, $NaAuCl_4 \cdot 2H_2O$, or a mixture thereof, or a silver precursor such as $AgNO_3$, but is not limited thereto.

For more details of the method for preparing Raman active particles, see Korean Patent Registration No. 10-2365091 B1 (Feb. 15, 2022).

The step of immobilizing a first receptor which may specifically bind to the substance to be detected on the surface of the Raman active particles of a-2) may be performed by mixing a first receptor with the Raman active particle dispersion prepared, and immobilization may be performed depending on the protocol known by the type of receptors, of course.

As a specific example, the first receptor is immobilized on the surface of the Raman active particles, and then a blocking solution including a blocking molecule may be used to further immobilize the blocking molecule on the surface of the Raman active particles on which the first receptor is not immobilized. Herein, the blocking molecule may be identical or similar to those described above.

As an exemplary example, the step of preparing a substrate on the surface of which a second receptor (capture antibody) which may specifically bind to the substance to be detected is positioned may be performed by any method without limitation as long as the method is known in the art.

Here, the second receptor specifically binds to the substance to be detected, but may bind to a site other than the site of the substance to be detected to which the first receptor binds, and since the first receptor and the second receptor are identical or similar to those described above, detailed description thereof will be omitted.

As an example, the substrate may be a metal such as gold, silver, platinum, palladium, nickel, aluminum, or copper or silicon, and may be surface-modified so that it may bind to the second receptor and the blocking molecular Herein, the blocking molecule may be identical or similar to those described above.

After manufacturing the Raman probe and preparing the substrate, a sample including the substance to be detected is brought into contact with the prepared substrate to capture the substance, and further brought into contact with the manufactured Raman probe to form an analysis structure to be capped.

The substance to be detected included in the sample is captured by binding to the second receptor primarily immobilized on the substrate, and then further binds to the first receptor immobilized on the Raman probe and is capped.

Herein, the sample including the substance to be detected may be applied on and contact with the substrate on which the second receptor is immobilized, and after a sufficient time has elapsed for the substance to be detected included in the sample to stably bind to the second receptor, a residual sample which does not bind to the second receptor, of the applied sample may be removed.

In addition, after the substance to be detected binds to the second receptor, a Raman probe dispersion is applied or the substance to be detected binding to the second receptor is immersed in the Raman probe dispersion, thereby bringing the substance to be detected into contact with the Raman probe. After a sufficient time has elapsed for the substance to be detected to stably bind to the first receptor immobilized on the Raman probe, an unreacted Raman probe may be removed.

Here, a dispersion medium of the Raman probe dispersion may be any material which does not chemically react with the Raman active particles and does not affect Raman measurement.

As an example, the dispersion medium may include a buffer solution such as a HEPES solution, a phosphate buffer (PB) solution, and a phosphate-buffered saline (PBS) solution, deionized water, and the like, but is not limited thereto.

As an example, removal of the residual sample of the sample applied on the substrate and the removal of unreacted Raman probe may be performed using a washing solution which does not adversely affect the substance to be detected and the Raman active particles. Herein, the washing solution may be the buffer solution described above, deionized water, and the like, but the present invention is not limited thereto.

As described above, the step of detecting Raman spectroscopy by performing Raman mapping based on a Raman spectrum detected by irradiating the analysis structure with an excitation light, the analysis structure being formed by bringing the sample including the substance to be detected into contact with the substrate and the Raman probe successively, may be performed.

As a specific example, the excitation light may be a near-infrared ray having a wavelength of 750 nm or more, specifically a near-infrared ray having a wavelength of 750 nm to 1500 nm, and more specifically a near-infrared ray having a wavelength of 750 nm to 1000 nm or 750 nm to 800 nm, and the excitation light output may be at a level of 1 mW to 90 mW, as an example, 1 mW to 10 mW.

Since the Raman mapping performed using the excitation light described above may be identical or similar to the description above, detailed description thereof will be omitted.

In an exemplary embodiment, a digital signal which allows quantitative analysis of the substance to be detected by a combination of a Raman signal intensity calculated from the Raman spectrum obtained in the step of detecting Raman spectroscopy and a digital count calculated from the Raman mapping may be obtained.

Here, the digital count is the same as the digital count described above, and may be the total number of pixels of which the Raman signal intensity in the Raman map obtained by the Raman mapping performed in a predetermined area is more than the background threshold.

As a specific example, the digital signal obtained in the step of obtaining a digital signal may be the product of the Raman signal intensity and the digital count.

Since the product value of the Raman signal intensity and the digital count is used as the digital signal which is an indicator of quantitative analysis, the substance to be detected may be accurately quantitatively detected over a large dynamic range, and also, a limit of detection to detect the substance to be detected at an extremely low concentration may be improved, and the reliability and the reproducibility for the quantitative detection of the substance to be detected may be significantly improved.

As a specific example, the relative standard deviation of the digital signal for the substance to be detected at an extremely low concentration in a range of 1 fM to 80 fM, specifically 1 fM to 50 fM, more specifically 1 fM to 30 fM, and still more specifically 1 fM to 10 fM may be 25% or less, 24% or less, 23% or less, 22% or less, 21% or less, 20% or less, 19% or less, 18% or less, 17% or less, 16% or less, 15% or less, or 14.5% or less, the relative standard deviation (% RSD) of the obtained digital signal which is an indicator of detection reliability of the substance to be detected.

Here, the digital signal may be a signal obtained by performing the detection experiment for the same substance to be detected 5 times or more, 10 times or more, 20 times or more, 30 times or more, 40 times or more, or 50 times or more.

That is, the detection method of a substance to be detected in the sample according to an exemplary embodiment of the present invention allows accurate and quantitative detection of the substance to be detected in a large dynamic range, and allows detection of the substance to be detected at an extremely low concentration with excellent reliability.

As a specific example, the limit of detection (LOD) of the substance to be detected which is detected using the detection method according to an exemplary embodiment of the present invention may be 1 fM or less, 0.9 fM or less, or 0.8 fM or less.

As described above, since the substance to be detected which may be accurately quantitatively detected in a large dynamic range with excellent reliability using the detection method according to an exemplary embodiment of the present invention is identical or similar to those described above, detailed description thereof will be omitted.

Hereinafter, the surface-enhanced Raman scattering sensing platform according to the present invention and the detection method of the substance to be detected using the same will be described in detail, with reference to the examples. However, the following examples are only a reference for describing the present invention in detail, and the present invention is not limited thereto and may be implemented in various forms.

In addition, unless otherwise defined, all technical terms and scientific terms have the same meanings as those commonly understood by a person skilled in the art to which the present invention pertains. The terms used herein are only for effectively describing a certain exemplary embodiment, and are not intended to limit the present invention.

Example 1

4 mL of a solution of spherical Au colloid (EM.GC50, BBI solution) having a diameter of 50 nm was centrifuged at 4000 rpm for 10 minutes to remove a supernatant, and then was mixed with 4 mL of a 0.1 mM bis(p-sulfonatophenyl)phenylphosphine dihydrate dipotassium salt (BSPP) solution to prepare an Au core dispersion having a molar concentration of 0.1 nM.

4 mL of the Au core dispersion and 16 μL of a 10 mM 4-nitrobenzenethiol (4-NBT) solution were mixed (the final concentration of 4-NBT was 40 μM), was sonicated for 10 minutes, and was centrifuged at 4000 rpm for 10 minutes to recover an Au core dispersion in which a self-assembled monolayer of 4-NBT which was a Raman reporter was formed.

To 5 mL of the recovered Au core dispersion in which the self-assembled monolayer of 4-NBT was formed, 5 mL of a 10 mM HEPES buffer solution at pH 6.5 and 1 mL of 5 mM $HAuCl_4$ (254169, Sigma-Aldrich) were added to prepare a reaction solution, which was stirred at 700 rpm for 30 minutes. At this time, the pH of the buffer solution was adjusted using 1 mM NaOH and 1 mM HCl.

Thereafter, the reaction solution was successively centrifuged at 4000 rpm for 10 minutes to remove the supernatant, 4 mL of 0.1 mM BSPP was mixed with the reaction solution from which the supernatant was primarily removed, and then centrifugation was performed at 3000 rpm for 10 minutes to secondarily remove the supernatant. Thereafter, 4 mL of 0.1 mM BSPP was further mixed with the reaction solution from which the supernatant was secondarily removed, centrifugation was performed five times at 2000 rpm for 10 minutes to remove the supernatant, and then 4 mL of deionized water was added to complete the reaction.

The finally obtained Raman active particles were added to 1 mL of a 50 mM HEPES buffer solution and the solution was stored at a temperature of 4° C. At this time, the obtained Raman active particles were named R10.

The thus-prepared Raman active particles were irradiated with an excitation light, Raman mapping was performed based on a Raman signal at 1333 $cm^{-1}$ detected in a 10 μm×10 μm mapping area size (1 μm mapping pitch), and product of the Raman intensity and the digital count calculated therefrom was used as a detection signal to perform Raman analysis.

Example 2

The process was performed in the same manner as in Example 1, except that 5 mL of 25 mM HEPES buffer solution at pH 6.5 and 1 mL of 5 mM $HAuCl_4$ (254169, Sigma-Aldrich) were added to a recovered 5 mL Au core dispersion in which the self-assembled monolayer of 4 NBT was formed to prepare a reaction solution, which was used to prepare Raman active particles, which were named R25.

Example 3

The process was performed in the same manner as in Example 1, except that 5 mL of 50 mM HEPES buffer solution at pH 6.5 and 1 mL of 5 mM $HAuCl_4$ (254169, Sigma-Aldrich) were added to a recovered 5 mL Au core dispersion in which the self-assembled monolayer of 4 NBT was formed to prepare a reaction solution, which was used to prepare Raman active particles, which were named R50.

Example 4

The process was performed in the same manner as in Example 1, except that 5 mL of 100 mM HEPES buffer solution at pH 6.5 and 1 mL of 5 mM $HAuCl_4$ (254169, Sigma-Aldrich) were added to a recovered 5 mL Au core dispersion in which the self-assembled monolayer of 4 NBT was formed to prepare a reaction solution, which was used to prepare Raman active particles, which were named R100.

Example 5

The process was performed in the same manner as in Example 1, except that 5 mL of 200 mM HEPES buffer solution at pH 6.5 and 1 mL of 5 mM $HAuCl_4$ (254169, Sigma-Aldrich) were added to a recovered 5 mL Au core dispersion in which the self-assembled monolayer of 4 NBT was formed to prepare a reaction solution, which was used to prepare Raman active particles, which were named R200.

Example 6

The process was performed in the same manner as in Example 1, except that 5 mL of 500 mM HEPES buffer solution at pH 6.5 and 1 mL of 5 mM $HAuCl_4$ (254169, Sigma-Aldrich) were added to a recovered 5 mL Au core dispersion in which the self-assembled monolayer of 4 NBT was formed to prepare a reaction solution, which was used to prepare Raman active particles, which were named R500.

Comparative Example 1

The process was performed in the same manner as in Example 3, except that Raman mapping was performed and the Raman intensity calculated therefrom was used as a detection signal to perform Raman analysis.

Comparative Example 2

The process was performed in the same manner as in Example 3, except that Raman mapping was performed and the digital count calculated therefrom was used as a detection signal to perform Raman analysis.

(Experimental Example 1) Analysis of Raman Active Particle Characteristics

The morphology properties and the optical properties of the Raman active particles prepared according to each preparation examples were compared and analyzed.

Figure 1B:
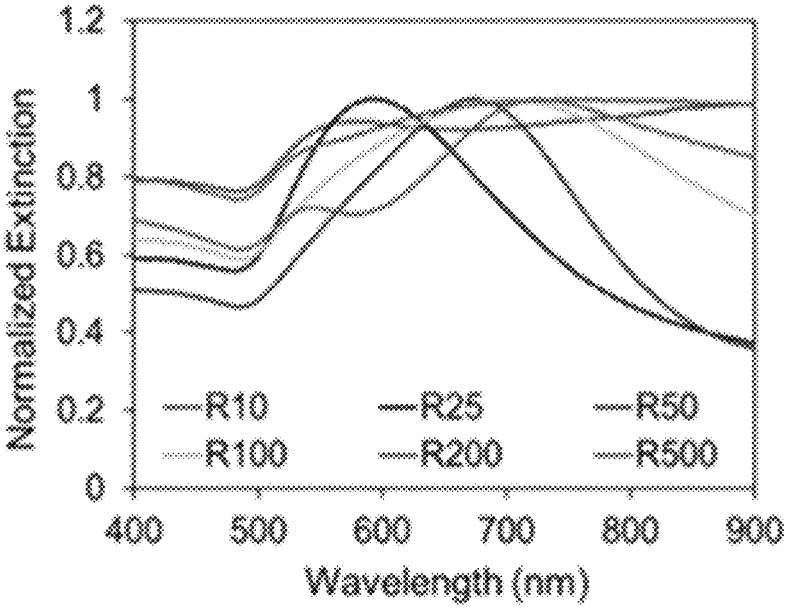
FIGS. 1B, 1C, and 1D are an ultraviolet-visible (UV-vis) extinction spectrum measured by UV-vis spectrometry, a size distribution and a maximum extinction wavelength of localized surface plasmon resonance (LSPR), and a drawing which compares and illustrates UV-vis extinction spectra of a Raman active particles (R50) of Example 3, an Au core particle, and an Au core particles in which a self-assembled monolayer of 4-NBT is formed, respectively.
Figure 1C:
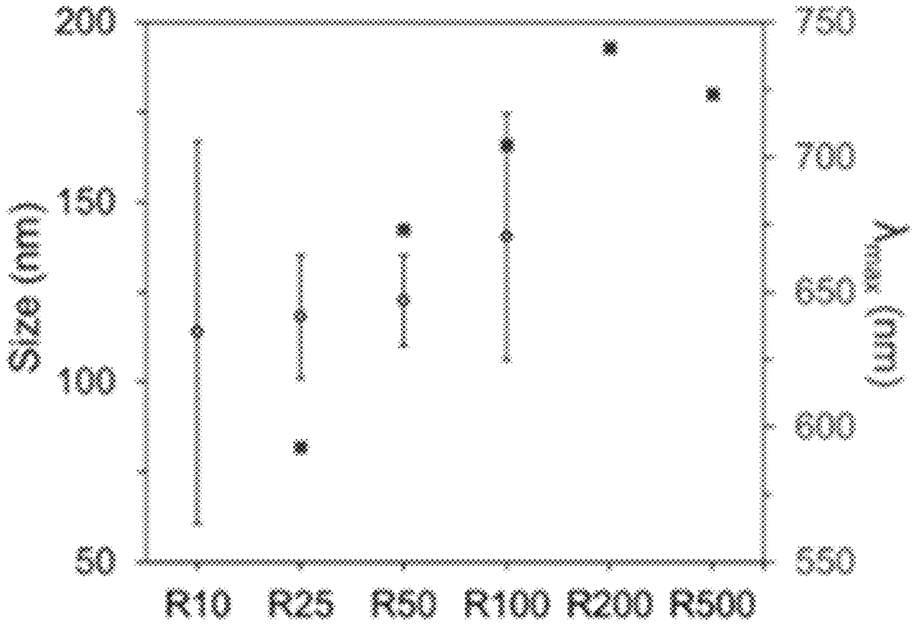
Figure 1D:
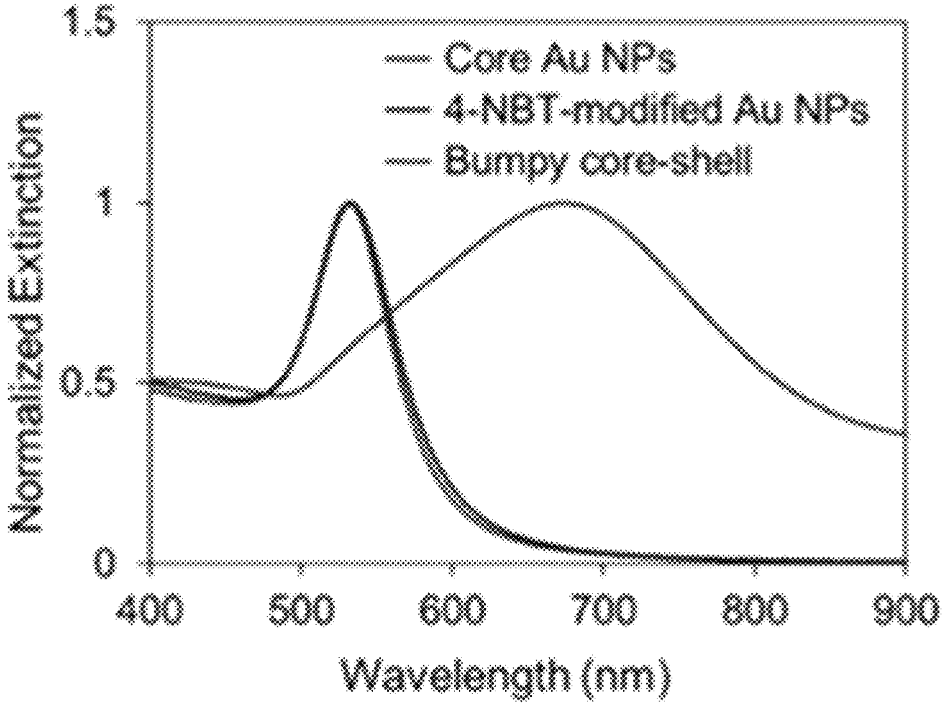

FIG. 1A is a drawing illustrating a scanning electron microscopic (SEM) image of Raman active particles prepared according to Examples 1 to 6, and FIGS. 1B, 1C, and 1D are an ultraviolet-visible (UV-vis) extinction spectrum measured by UV-vis spectrometry, a size distribution and a maximum extinction wavelength of localized surface plasmon resonance (LSPR), and a drawing which compares and illustrates UV-vis extinction spectra of a Raman active particles (R50) of Example 3, an Au core particle, and an Au core particles in which a self-assembled monolayer of 4-NBT is formed, respectively.

Referring to FIG. 1A, it was observed that the shell structure of the Raman active particles of Examples 1 to 4 showed similar shapes to a spherical shape, but the shell structure of the Raman active particles of Examples 5 and 6 has a spike-like shape. In addition, in Examples 2 to 4, it was observed that an anisotropically grown shell structure completely and uniformly enclosed the entire core, but in Examples 1, 5, and 6, it was confirmed that the shell structure was not uniform and did not completely enclose the core, and thus, an incomplete shell structure was formed.

As illustrated in FIG. 1B, it was shown that the optical properties appeared different by the morphology properties of the Raman active particles described above. Specifically, it was confirmed that the LSPR peaks of Examples 2 to 6 were red-shifted gradually based on the LSPR peak of Example 1, and, in particular, it was shown that the UV-vis extinction spectra of Examples 1, 5, and 6 were relatively broad spectra. This was due to the fact that as shown in FIG. 3C, in Examples, 1, 5, and 6, the size uniformity was relatively poor and the Raman active particles were aggregated.

Furthermore, referring to FIG. 1D, it was shown that the optical properties changed during the process of synthesis of the Raman active particles (R50) of Example 3 in which the self-assembled monolayer of 4-NBT was formed using the Au core particles as a starting material, and then the shell structure was formed. Specifically, it was observed that the maximum extinction wavelengths of LSPR of the Au core particles and the Au core particles on which the self-assembled monolayer of 4-NBT was formed were 532 nm and 533 nm, respectively, which were very similar, but the maximum extinction wavelength of LSPR of the finally synthesized Raman active particles (R50) of Example 3 was rapidly increased to 674 nm.

The Raman active particles of Example 2 (R25), Example 3 (R50), and Example 4 (R100) were more closely analyzed, considering the morphology and optical properties of the Raman active particles described above.

Figure 2A:
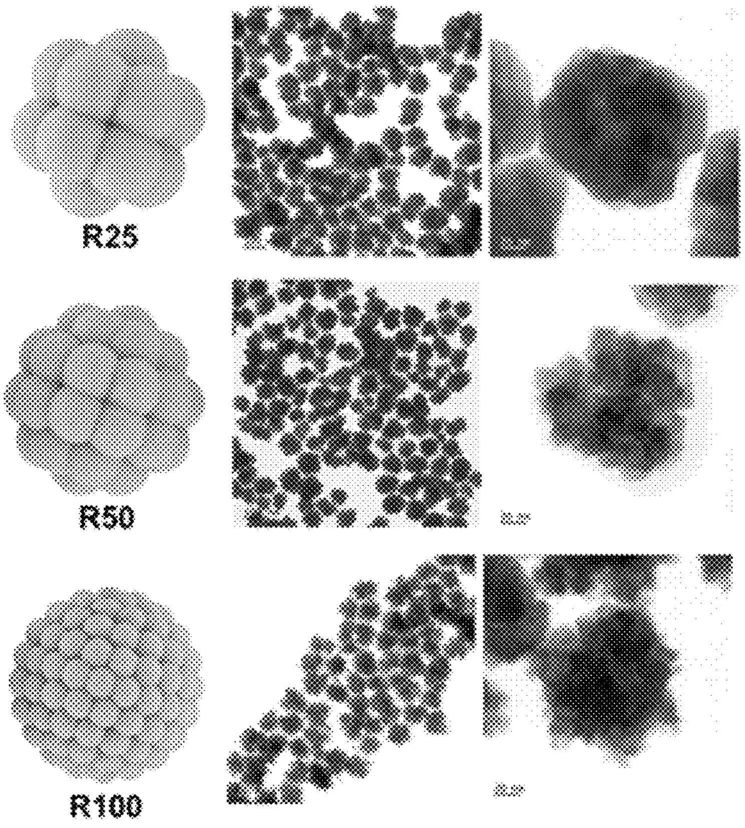
FIGS. 2A and 2B are a schematic diagram and transmission electron microscopic (TEM) images at low and high magnifications of Raman active particles of Example 2 (R25), Example 3 (R50), and Example 4 (R100), and a drawing illustrating size distributions of the Raman active particles having a core-shell structure and fine particles (bump) forming a shell, respectively.
Figure 2B:
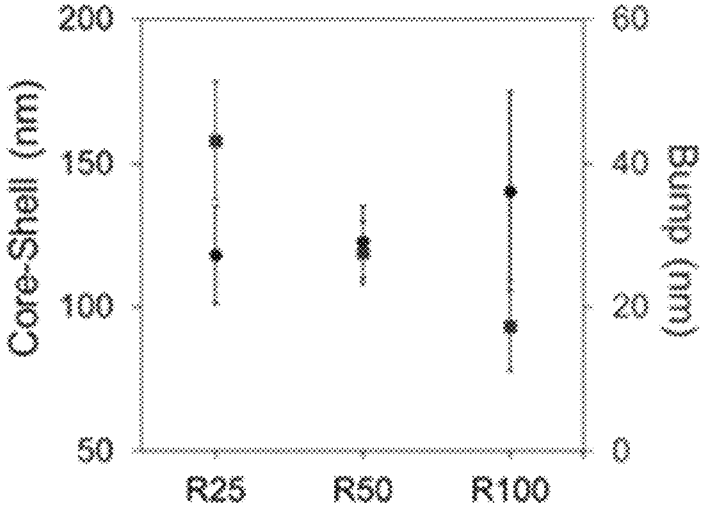

FIGS. 2A and 2B are a schematic diagram and transmission electron microscopic (TEM) images at low and high magnifications of Raman active particles of Example 2 (R25), Example 3 (R50), and Example 4 (R100), and a drawing illustrating size distributions of the Raman active particles having a core-shell structure and fine particles (bump) forming a shell, respectively.

Referring to FIGS. 2A and 2B, it was confirmed that the self-assembled monolayer of the Raman reporter was positioned between the Au core and the polycrystalline Au shell formed of Au fine particles, and uniform nanogaps having a thickness of 0.8 nm were formed in the entire area of the particles.

In addition, it was shown that the Raman active particles of Examples 2, 3, and 4, that is, the Raman active particles having a core-shell structure, had an average size of 118.1 nm, 122.6 nm, and 140.4 nm, respectively, and the fine particles (bump) had an average size of 43.2 nm, 27.5 nm, and 17.4 nm, respectively. In particular, in Example 3, it was observed that the structural uniformity of the shell, the size of the Raman active particles of the core-shell structure, and fine particle (bump) size uniformity were the best.

Additionally, surface-enhanced Raman scattering (SERS) activity was evaluated under excitation light irradiation conditions at wavelengths of 532 nm, 633 nm, and 780 nm.

Figure 3A:
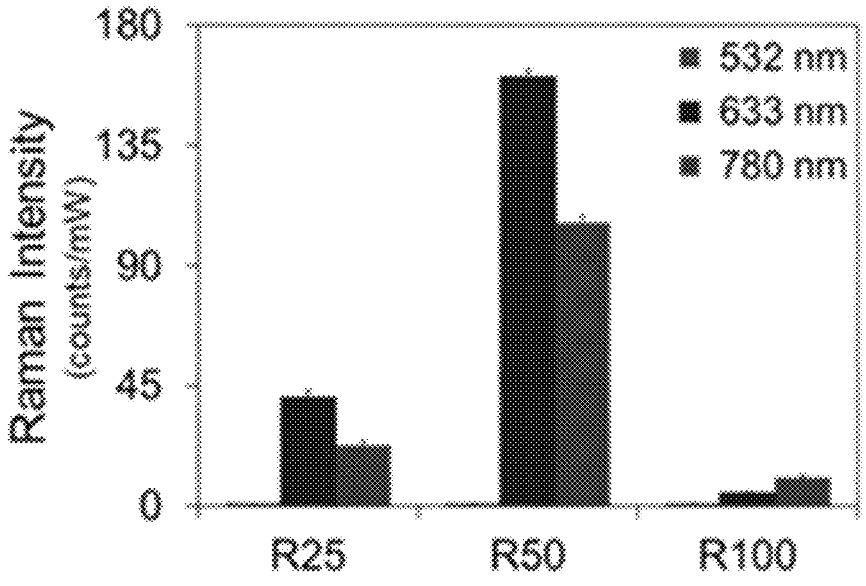
FIGS. 3A and 3B are a drawing which compares and illustrates Raman intensities which are peak intensities in at a 1333 $cm^{-1}$ Raman shift which is a specific peak of a 4-NBT Raman reporter for the Raman active particles of Example 2, Example 3, and Example 4, and a drawing illustrating light stability test results for an excitation light at wavelengths of 633 nm and 780 nm for Example 3, respectively.
Figure 3B:
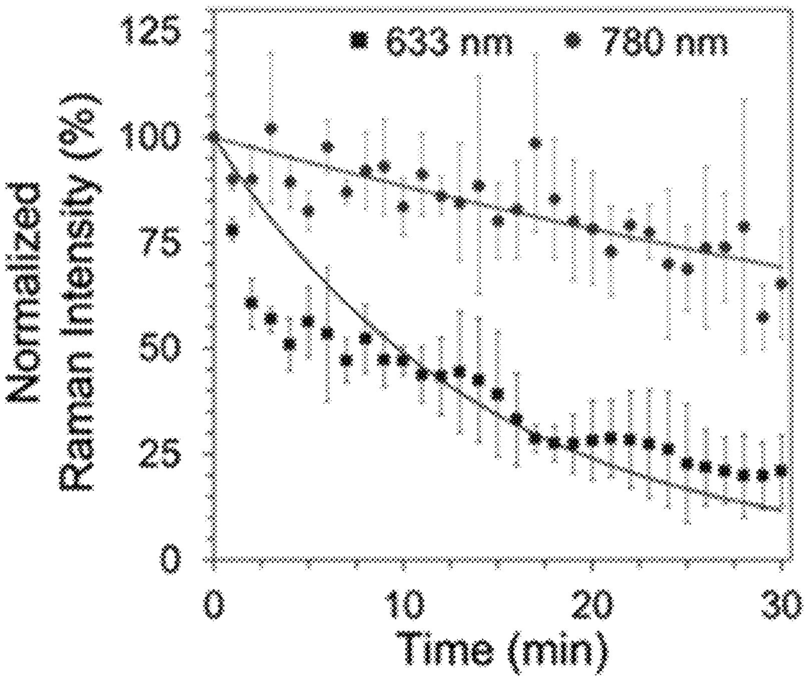

FIGS. 3A and 3B are a drawing which compares and illustrates Raman intensities which are peak intensities in at a 1333 $cm^{-1}$ Raman shift which is a specific peak of a 4-NBT Raman reporter for the Raman active particles of Example 2, Example 3, and Example 4, and a drawing illustrating light stability test results for an excitation light at wavelengths of 633 nm and 780 nm for Example 3, respectively.

At this time, for SERS activation evaluation, the Raman active particles were dispersed in an aqueous solution so that the concentration of each Raman active particle was 10 pM, and 532 nm wavelength laser at 10 mW, 633 nm wavelength laser at 8 mW, and 780 nm wavelength laser at 24 mW were used as the excitation light and were irradiated for 10 seconds.

Referring to FIGS. 3A and 3B, it was observed that all of the Raman active particles of Examples 2, 3, and 4 showed little SERS activity to the excitation light at a 532 nm wavelength, and Example 3 showed the SERS activity most strongly to the excitation lights at 633 nm and 780 nm wavelengths.

In particular, the Raman intensity was showed most strongly to the excitation light at a 633 nm wavelength, but as shown in FIG. 3B, the light stability was confirmed to be lower as compared with the excitation light at a 780 nm wavelength.

(Experimental Example 2) Evaluation of Surface-Enhanced Raman Scattering (SERS) Sensing at a Single Particle Level Considering the morphology properties, the size uniformity, the SERS properties, and the light stability of the Raman active particles evaluated before, the Raman active particles of Example 3 were used to evaluate SERS sensing possibility at a single particle level under the conditions of irradiation of a 780 nm excitation light.

Figure 4A:
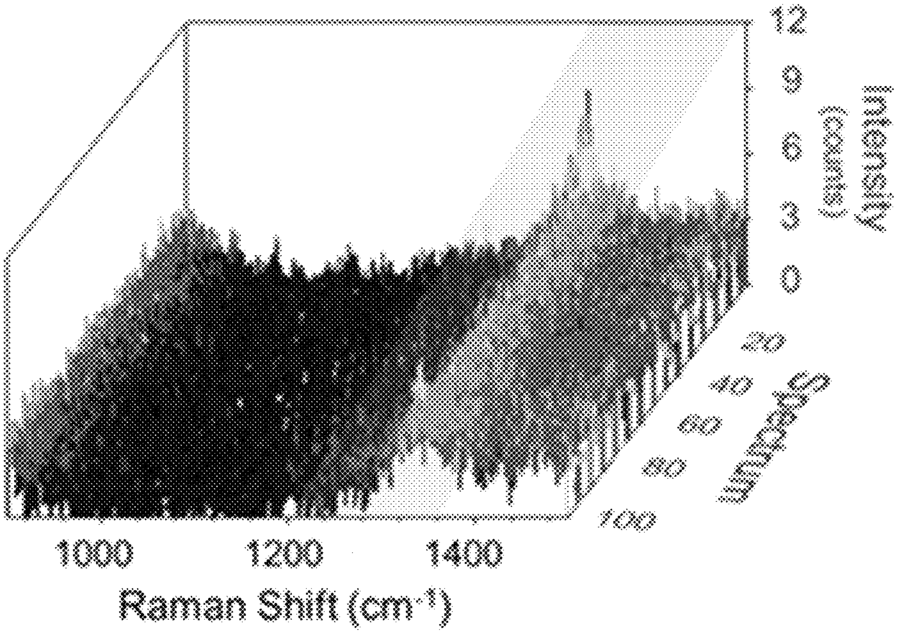
FIGS. 4A, 4B, and 4C are drawings illustrating a Raman spectrum, a Raman intensity, and a Raman intensity distribution measured by Raman analysis for Raman active particles at a concentration of 1 fM dispersed in an aqueous solution, respectively.
Figure 4B:
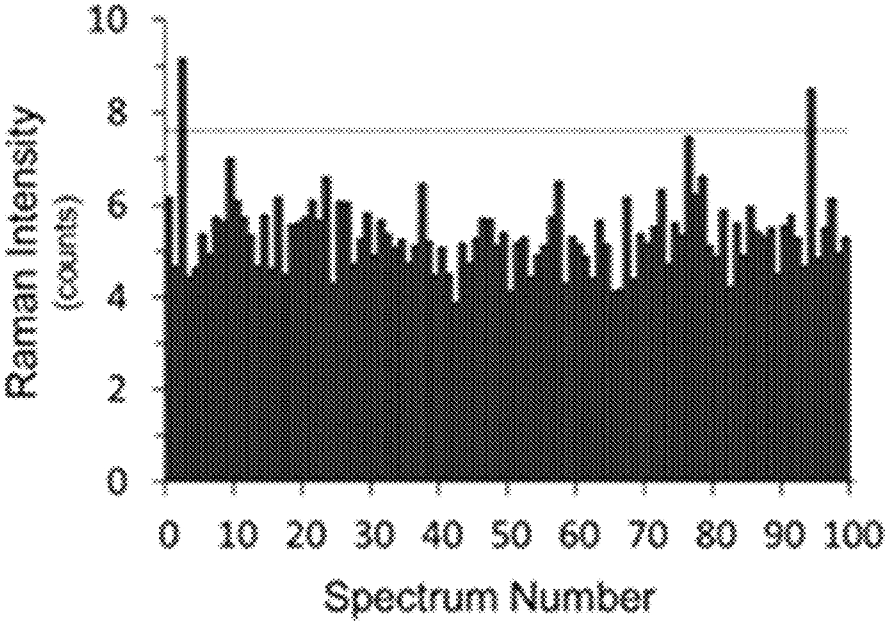
Figure 4C:
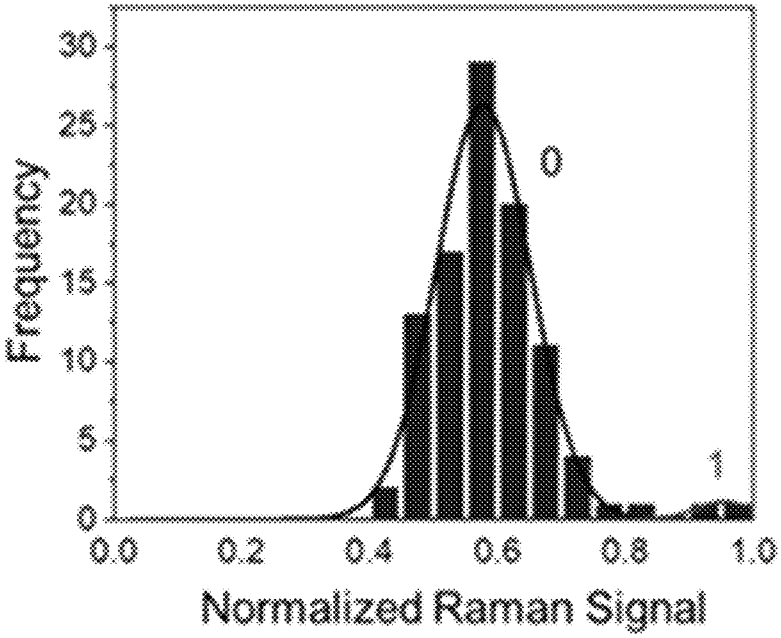

FIGS. 4A, 4B, and 4C are drawings illustrating a Raman spectrum, a Raman intensity, and a Raman intensity distribution measured by Raman analysis for Raman active particles at a concentration of 1 fM dispersed in an aqueous solution, respectively.

At this time, Raman analysis was performed by measuring the Raman spectrum and the Raman intensity corresponding to each pixel from the mapping image of the 1333 $cm^{-1}$ Raman signal detected from a mapping area size of 10 μm×10 μm (1 μm mapping pitch), that is, from the Raman mapping image composed of a total of 100 pixels, using a 780 nm wavelength laser at 24 mW.

Referring to FIG. 4A, it was shown that there was a specific peak of 4-NBT Raman reporter in the Raman active particles at an extremely low concentration of 1 fM. In order to more clarify this, it was confirmed that only 2% of the total Raman spectrum was more than the background threshold marked with a dotted line, as shown in FIG. 4B.

At this time, the background threshold was set using the sum of maximum Raman intensities obtained by Raman analysis performed for a reagent which did not include the Raman active particles and the standard deviation.

Specifically, the sum of the maximum background Raman intensity detected from the Raman mapping image composed of a total of 100 pixels obtained by Raman analysis performed using a reagent including no Raman active particle and the background standard deviation which is the standard deviation of the Raman intensity detected in each pixel was set as the background threshold.

Referring to FIG. 4C, two Gaussian distributions in which the probability that the Raman active particles were found was 0 or 1 in the normalized Raman intensity distribution are shown. In particular, since each Gaussian distribution did not overlap each other, it was confirmed that SERS sensing at a single particle level was possible.

Additionally, when a dynamic range which is a detection section where the substance to be detected was more accurately quantitatively measurable was expanded, in order to evaluate whether quantitative detection was possible, the Raman analysis was performed for the sample having a Raman active particle concentration of 1 fM to 10 pM.

Figure 5A:
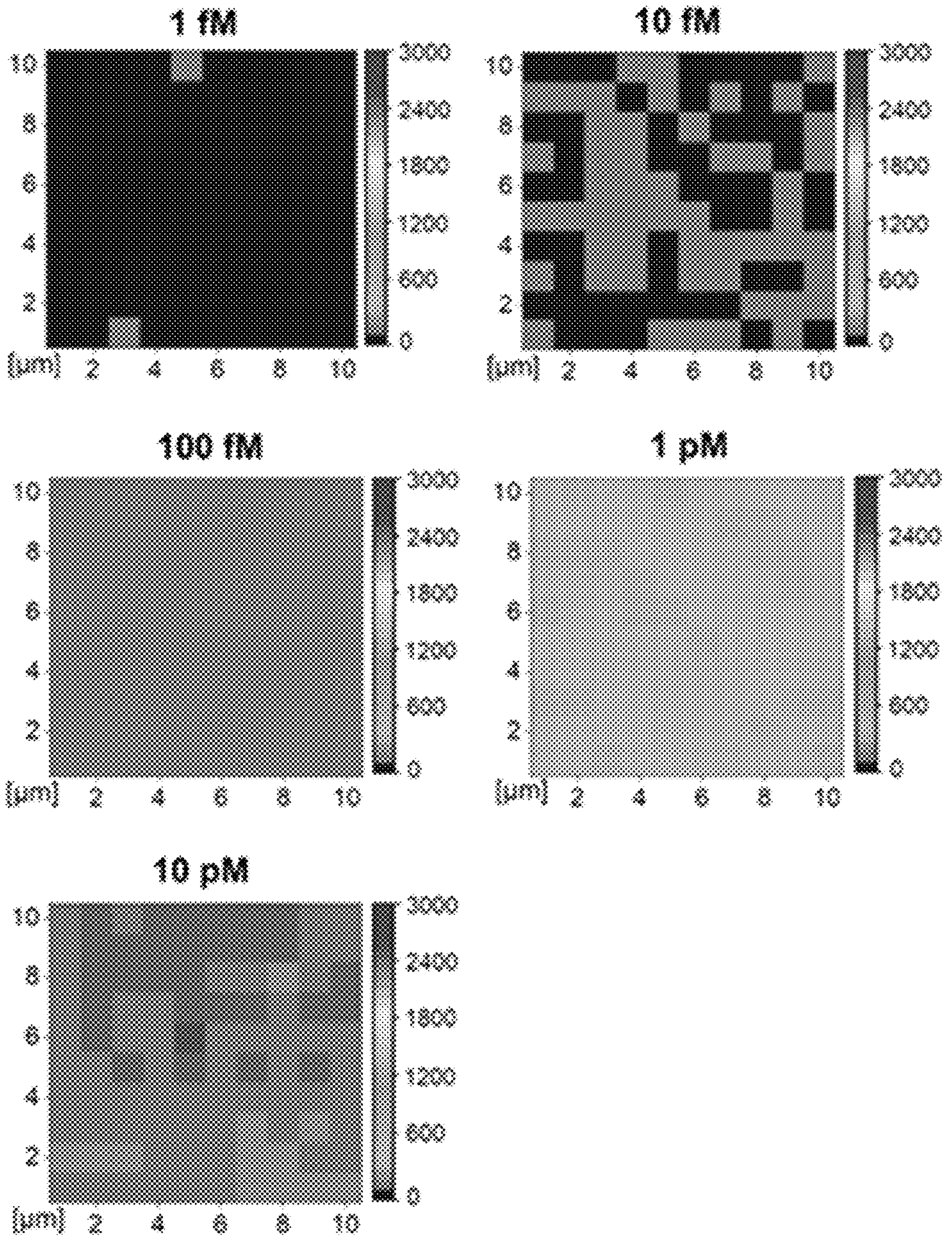
FIGS. 5A and 5B are drawings illustrating Raman mapping images and a Raman spectrum measured by Raman analysis performed Raman active particles at concentrations of 1 fM, 10 fM, 100 fM, 1 pM, and 10 pM, respectively.
Figure 5B:
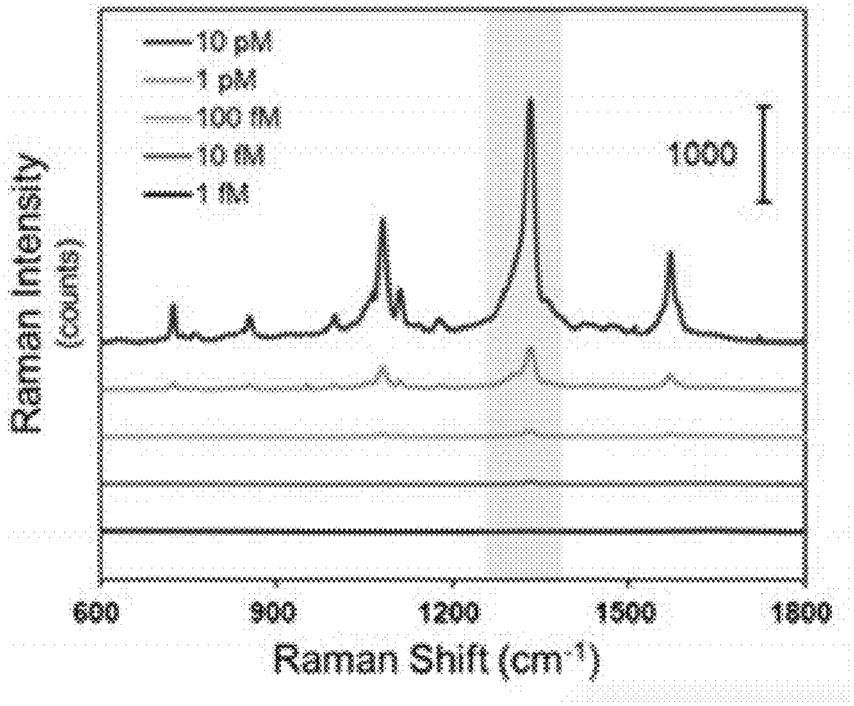
Figure 5C:
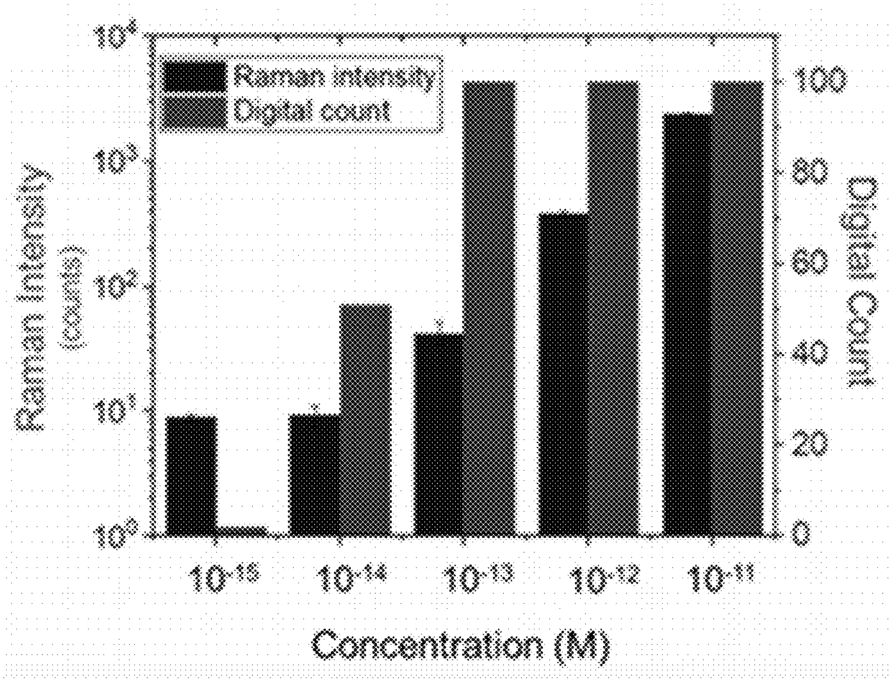
FIG. 5C is a drawing illustrating a Raman intensity depending on a Raman active particle concentration calculated from a Raman spectrum and a digital count depending on Raman active particle concentration calculated from a Raman mapping image.
Figure 5D:
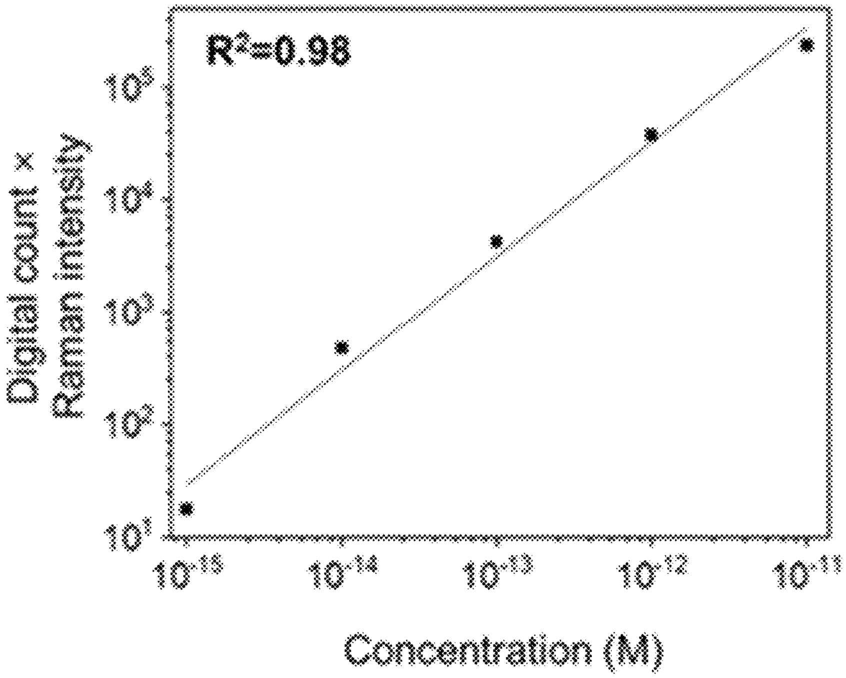
FIG. 5D is a drawing illustrating a correlation of a product value of a Raman active particle concentration, a Raman intensity, and a digital count.

FIGS. 5A and 5B are drawings illustrating Raman mapping images and a Raman spectrum measured by Raman analysis performed Raman active particles at concentrations of 1 fM, 10 fM, 100 fM, 1 pM, and 10 pM, respectively, FIG. 5C is a drawing illustrating a Raman intensity depending on a Raman active particle concentration calculated from a Raman spectrum and a digital count depending on Raman active particle concentration calculated from a Raman mapping image, and FIG. 5D is a drawing illustrating a correlation of a product value of a Raman active particle concentration, a Raman intensity, and a digital count.

At this time, the digital count was set as the total number of pixels of which the Raman intensity was more than the background threshold in the Raman mapping image composed of a total of 100 pixels.

As shown in FIG. 5A, the Raman mapping image had pixels composed of different colors from each other depending on the Raman intensity, and in the case of the pixel having the Raman intensity of the background threshold or less, it was marked in dark blue.

Referring to FIG. 5C, it was shown that in the case of being based on the Raman intensity (Comparative Example 1), there was a limit to quantitatively detect the Raman active particles at a relatively low concentration of $10^{-14}$ M or less, but in the case of being based on the digital count (Comparative Example 2), there was a limit to quantitatively detect the Raman active particles of $10^{-13}$ M or more.

However, as shown in FIG. 5D, the product value of the Raman intensity and the digital count showed an excellent linear relationship with the concentration of the Raman active particles. That is, the Raman active particles from those at a concentration of $10^{-15}$ M to those at a concentration of $10^{-11}$ M may be accurately quantitatively detected, using the product of the Raman intensity and the digital count as an indicator.

In general, in the case of SERS-based detection signal, reliability degradation based on the detection probability variability is often observed at a low concentration. Thus, in order to further evaluate the detection reliability at a low concentration, the Raman analysis was repeated 30 times for the Raman active particles at each of the concentrations of 1 fM and 10 fM, and each of the Raman intensity calculated from the Raman mapping image and the product of the Raman intensity and the digital count was applied as an independent detection signal and analyzed.

It was observed that the relative standard deviations of the detection signal based on the Raman intensity were 52.84% and 28.45%, respectively, in the Raman active particles at concentrations of 1 fM and 10 fM, which showed that the reproducibility was rapidly decreased at lower concentrations.

However, it was observed that the relative standard deviations of the detection signal based on the product of the Raman intensity and the digital count were 14.21% and 12.12%, respectively, in the Raman active particles at concentrations of 1 fM and 10 fM, which showed improved reproducibility.

In addition, it was confirmed that when the concentration of the Raman active particles was 10 pM or more, the relative standard deviation of the detection signal based on the product of the Raman intensity and the digital count was 2.5% or less, which showed excellent reproducibility.

It was shown therefrom that the detection signal based on the product of the Raman intensity and the digital count allows more accurate quantitative detection of the Raman active particles at an extremely low concentration with excellent reliability, as compared with the detection method based on the Raman intensity.

Example 7

The Raman active particles (R50) of Example 3 were washed, the Raman active particles which were resuspended in a 5 mM borate buffer solution were reacted with a first receptor (detection antibody) solution including SARS-CoV-2 Spike (S) antibody (40150-D003 and 40150-D001) at a concentration of 1 μg/mL for 2 hours, and then mixed with a prepared first bovine serum albumin (BSA) blocking solution (3% BSA, 0.05% Tween 20, 0.01×PB (phosphate buffer solution)).

Thereafter, the mixed solution was centrifuged at 2000 μm for 10 minutes to resuspend the Raman active particle pellet in which the first receptor and the blocking molecule were formed in an analysis buffer solution (1% BSA, 0.05% Tween 20, 0.01×PB) to prepare a Raman probe.

A silicon substrate (5 mm×5 mm) was washed for 30 minutes with a Piranha solution ($H_2SO_4$:$H_2O_2$=3:1), cleaned with deionized water, and plasma-treated. Thereafter, a 2% (3-Aminopropyl)triethoxysilane (APTES) solution dissolved in ethanol was used to treat the surface of the plasma-treated silicon substrate at 120° C. for 2 hours, and then baked to form a organosilane layer which was densely packed on a silicon substrate.

Subsequently, a 2.5% glutaraldehyde solution was used to modify the surface of the silicon substrate on which the organosilane layer was formed and then washed with a phosphate-buffered saline (PBS) buffer solution.

Thereafter, a second receptor (detection antibody) solution including SARS-CoV-2 Spike (S) antibody (40150-D003 and 40150-D001) at a concentration of 10 μg/mL was reacted on the surface-modified silicon substrate at 4° C. overnight to form a second receptor on the silicon substrate, and then a second bovine serum albumin (BSA) blocking solution (3% BSA, 0.05% Tween 20, 1×PBS) was used to prepare a silicon substrate including the passivated second receptor.

In order to form an analysis structure for sandwich immunoassay, S protein (SARS-CoV-2 S antigen (40592-V08B)) at a concentration of 100 fg/mL to 1 μg/mL was brought into contact with the previously prepared silicon substrate for 3 hours, and then washed with a PBS buffer solution. Subsequently, the prepared Raman probe was contacted further and incubated at room temperature for 2 hours, washed with 0.01×PB, and washed again with deionized water twice to form an analysis structure.

Subsequently, in order to detect the substance to be detected, SARS-CoV-2 S, a 780 nm wavelength laser at 5 mW was used to irradiate an excitation light for 2 seconds, Raman mapping was performed based on a Raman signal at 1333 $cm^{-1}$ detected in a 10 μm×10 μm mapping area size (1 μm mapping pitch), and product of the Raman intensity and the digital count calculated therefrom was used as a detection signal to perform Raman analysis.

Figure 6A:
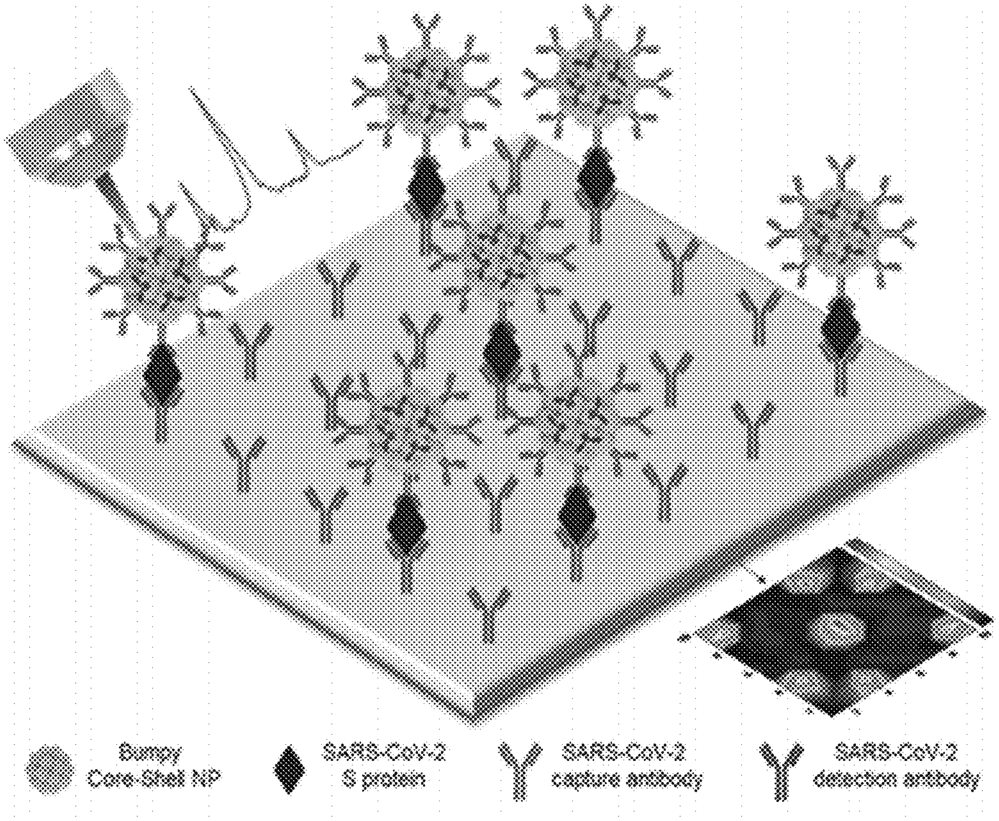
FIGS. 6A and 6B are a schematic diagram of a platform which may quantitatively detect a substance to be detected according to an exemplary embodiment of the present invention, and a drawing illustrating a detection signal calculated therefrom, respectively.
Figure 6B:
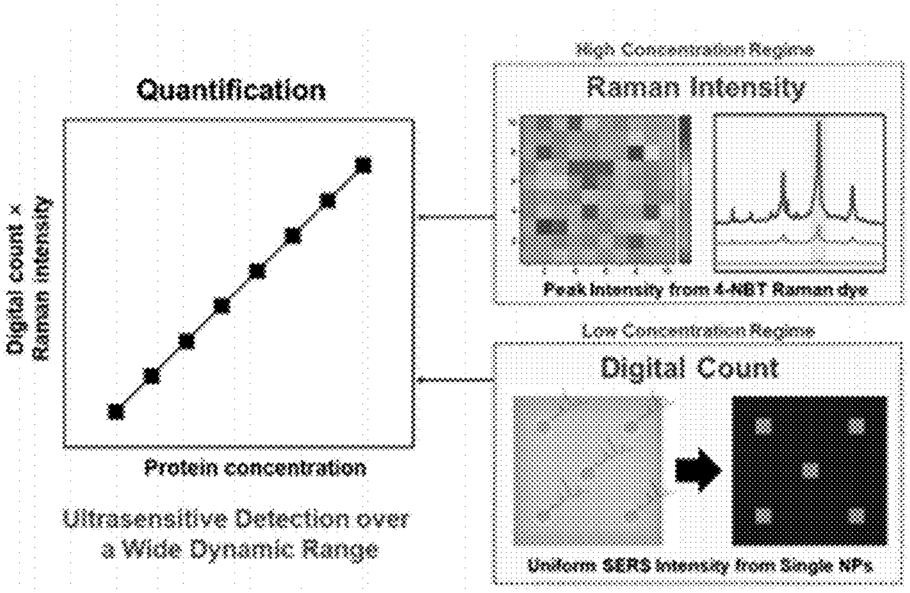

FIGS. 6A and 6B are a schematic diagram of a platform which may quantitatively detect a substance to be detected according to an exemplary embodiment of the present invention, and a drawing illustrating a detection signal calculated therefrom, respectively.

Example 8

The process was performed in the same manner as in Example 7, except that S RBD (N501Y)-His Recombinant protein at a concentration of 10 ng/mL was used to form an analysis structure.

Example 9

The process was performed in the same manner as in Example 7, except that S RBD (E484K)-His Recombinant protein at a concentration of 10 ng/mL was used to form an analysis structure.

Example 10

The process was performed in the same manner as in Example 7, except that S RBD (T478K)-His Recombinant protein at a concentration of 10 ng/mL was used to form an analysis structure.

Comparative Example 3

An enzyme-linked immunosorbent assay (ELISA) was used to detect S protein (SARS-CoV-2 S antigen (40592-V08B)) at a concentration of 100 fg/mL to 1 μg/mL.

Figure 7A:
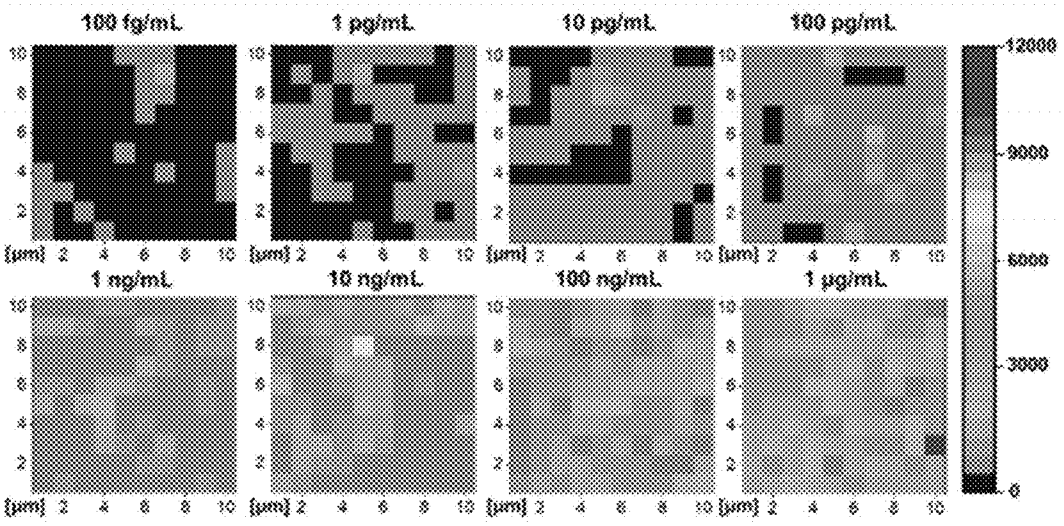
FIGS. 7A and 7B are drawings illustrating Raman mapping images and a Raman spectrum obtained by Raman analysis of Example 7, respectively.
Figure 7B:
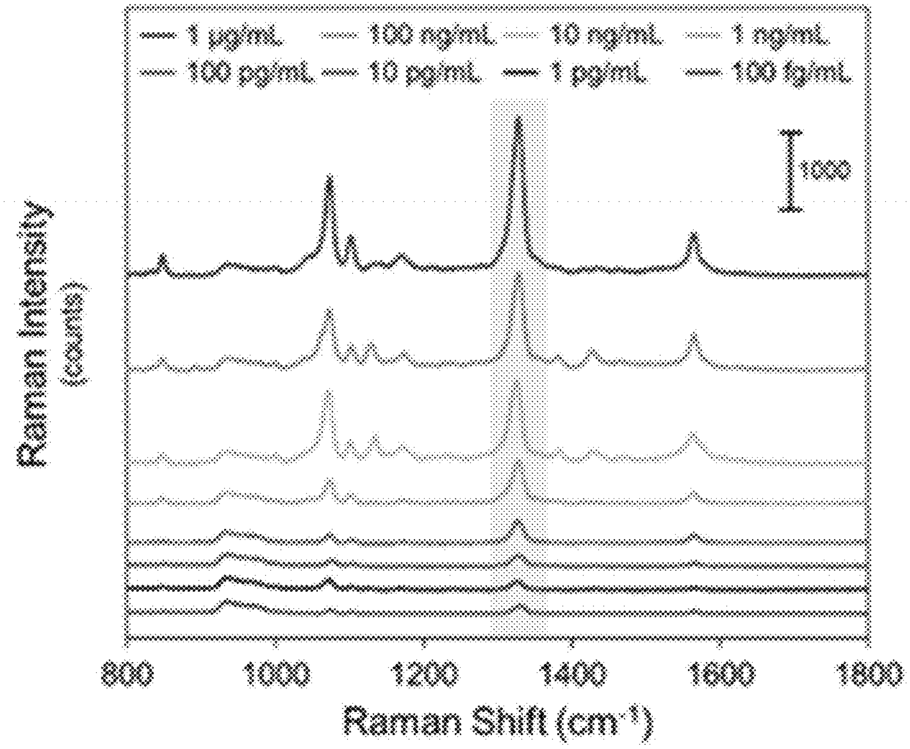
Figure 7C:
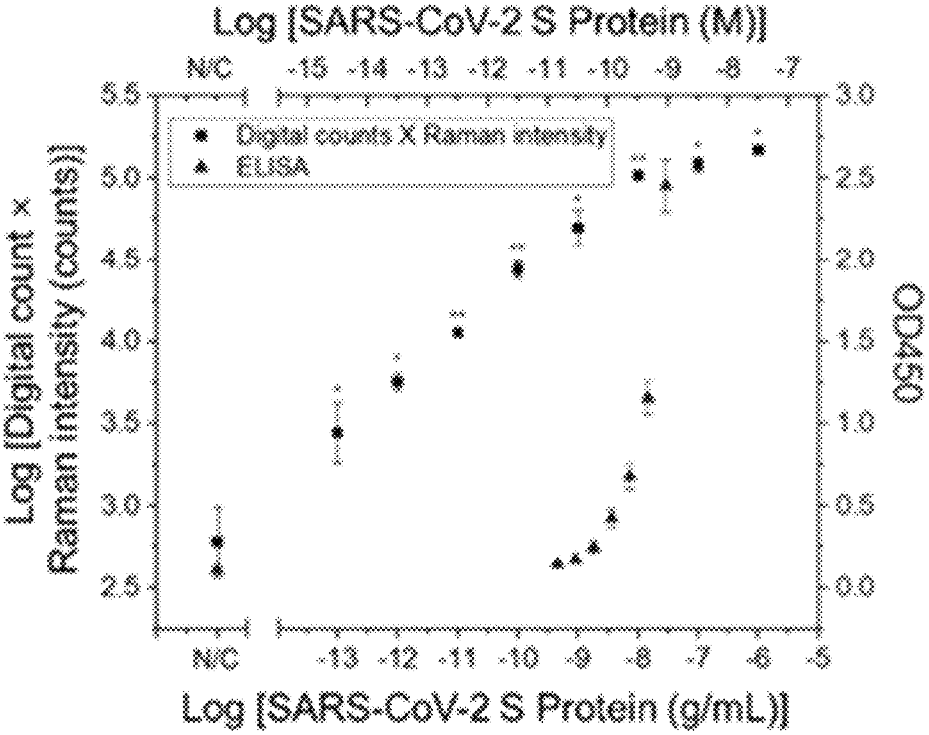
FIG. 7C is a drawing which compares and illustrates detection results of SARS-CoV-2 S protein performed in accordance with Example 7 and Comparative Example 3.

(Experimental Example 3) Comparison and Analysis of Results of Detecting Substance to be Detected FIGS. 7A and 7B are drawings illustrating Raman mapping images and a Raman spectrum obtained by Raman analysis of Example 7, respectively, and FIG. 7C is a drawing which compares and illustrates detection results of SARS-CoV-2 S protein performed in accordance with Example 7 and Comparative Example 3.

Referring to FIG. 7C, it was shown that the detection signal of SARS-CoV-2 S protein performed according to Example 7 was detected with a very excellent linear relationship in a large concentration range from $3.7\times10^{-5}$ M to $3.7\times10^{-8}$ M. In addition, it was observed that the limit of detection (LOD) was at a level of $7.1\times10^{-16}$ M ($1.9\times10^{-14}$ g/mL), which was significantly better than the limit of detection of SARS-CoV-2 S protein (about 10 pM) performed according to Comparative Example 3.

That is, it is shown that in detecting the target substance which is SARS-CoV-2 S protein, when the analysis is performed according to Example 7, an excellent limit of detection to detect a 104 times (4 orders of magnitude) lower concentration of the target substance is shown, and also, the target substance may be accurately quantitatively measured in a $10^5$ times (5 orders of magnitude) larger dynamic range, as compared with Comparative Example 3.

In addition, it was confirmed that the relative standard deviation of the detection signal based on the product of the Raman intensity and the digital count appears at a substantially similar level to the experimental results performed before.

Figure 8A:
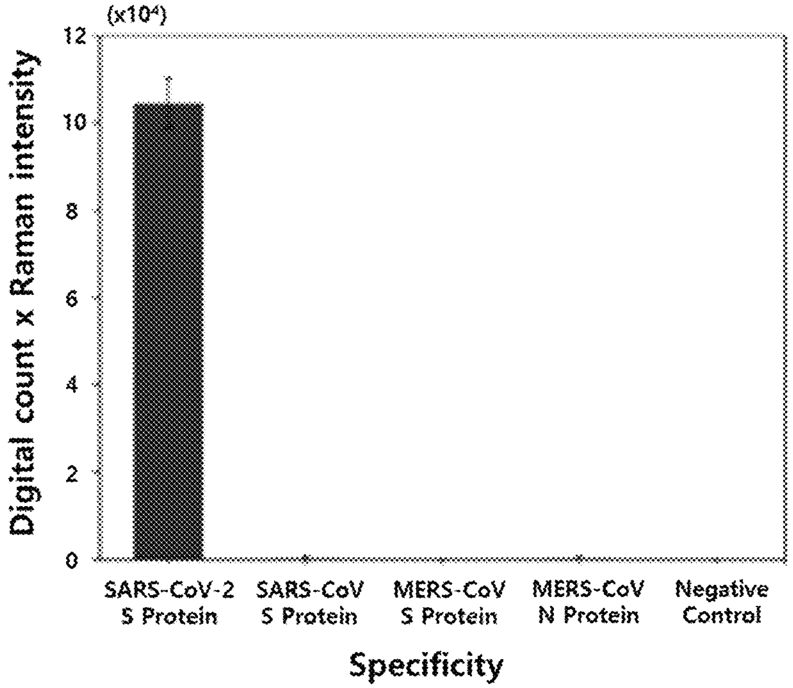
FIGS. 8A and 8B are a drawing illustrating detection specificity evaluation results of SARS-CoV-2 S protein and a drawing illustrating detection performance evaluation results of a variant of SARS-CoV-2 virus, respectively.

Additionally, in order to evaluate the detection specificity for SARS-CoV-2 S protein, the detection results for SARS-CoV S protein, MERS-CoV S protein, and MERS-CoV N protein which are other betacorona viruses were compared, and the results are shown in FIG. 8A.

At this time, the analysis was performed with the concentrations of the proteins being all identically 10 ng/mL.

As illustrated in FIG. 8A, it was shown that a limitedly strong detection signal was detected for SARS-CoV-2 S protein, and thus, the analysis method according to Example 1 had high selectivity to the target substance.

Figure 8B:
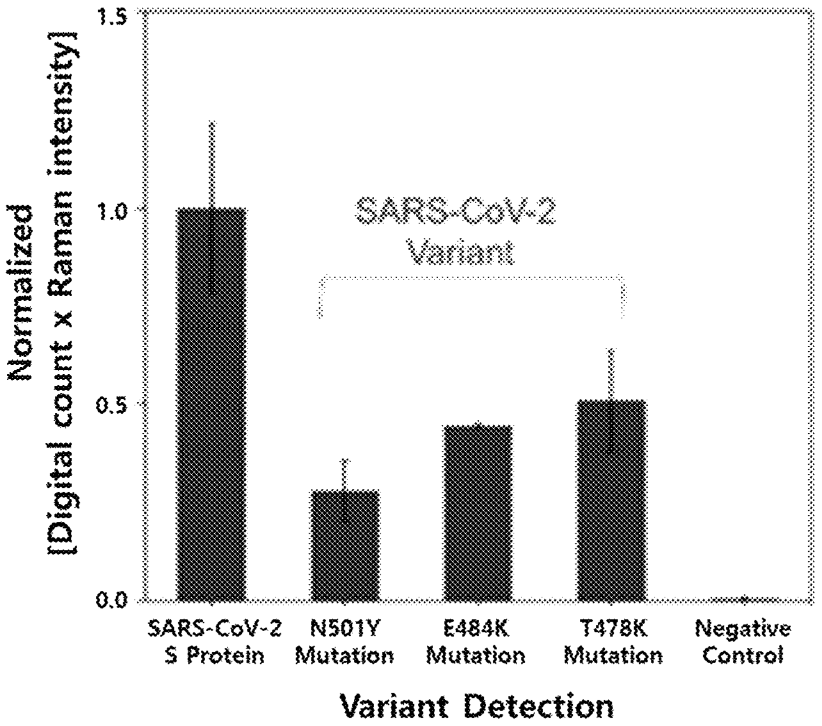

Furthermore, the detection performance for the variant of SARS-CoV-2 virus which was performed by the detection method according to an exemplary embodiment of the present invention was further evaluated, and the results are shown in FIG. 8B. As shown in FIG. 8B, it was confirmed that N501Y, E484K, and T478K variant proteins may be also detected by the detection method according to an exemplary example of the present invention.

The digital surface-enhanced Raman scattering (SERS) sensing platform of the present invention includes: a surface-enhanced Raman scattering (SERS) active reagent which includes Raman active particles including a spherical plasmonic metal core, a plasmonic metal shell having a surface unevenness, and a self-assembled monolayer including a Raman reporter positioned between the core and the shell; a Raman spectroscopic detection unit which performs Raman mapping based on a Raman spectrum which is detected by irradiating the active reagent with an excitation light; and a digital signal analysis unit which analyzes a quantitative detection signal of a substance to be detected by a combination of a Raman signal intensity calculated from the Raman spectrum and a digital count calculated from the Raman mapping, thereby quantitatively detecting the substance to be detected with excellent reliability and reproducibility, and improving the limit of detection (LOD) of the substance to be detected in a large dynamic range.

Hereinabove, although the present invention has been described by the specific matters and specific exemplary embodiments, they have been provided only for assisting in the entire understanding of the present invention. Therefore, the present invention is not limited to the exemplary embodiments, and various modifications and changes may be made by those skilled in the art to which the present invention pertains from this description.

Therefore, the spirit of the present invention should not be limited to the above-described exemplary embodiments, and the following claims as well as all modifications equal or equivalent to the claims are intended to fall within the scope and spirit of the invention.

What is claimed is:

1. A digital surface-enhanced Raman scattering (SERS) sensing platform comprising:

a surface-enhanced Raman scattering (SERS) active reagent which includes Raman active particles including a spherical plasmonic metal core, a plasmonic metal shell having a surface unevenness, and a self-assembled monolayer including a Raman reporter positioned between the core and the shell;

a Raman spectroscopic detection unit which performs Raman mapping based on a Raman spectrum which is detected by irradiating the active reagent with an excitation light; and a digital signal analysis unit which analyzes a quantitative detection signal of a substance to be detected by a combination of a Raman signal intensity calculated from the Raman spectrum and a digital count calculated from the Raman mapping;

wherein the digital count is a total number of pixels of which the Raman signal intensity is more than a background threshold in a Raman map obtained by the Raman mapping, wherein the background threshold is set using a sum of maximum Raman intensities obtained by Raman analysis performed for a reagent which does not include the Raman active particles and a background standard deviation, which is a standard deviation of the Raman intensity detected in each pixel, and wherein the quantitative detection signal is a product of the Raman signal intensity and the digital count.

2. The digital surface-enhanced Raman scattering (SERS) sensing platform of claim 1, wherein the plasmonic metal shell includes plasmonic metal fine particles having an average size of 0.3D to 0.6D, based on a diameter (D) of the metal core, and has surface unevenness due to the plasmonic metal fine particles.

3. The digital surface-enhanced Raman scattering (SERS) sensing platform of claim 1, wherein the self-assembled monolayer has a thickness of 0.5 to 1.5 nm.

4. The digital surface-enhanced Raman scattering (SERS) sensing platform of claim 1, wherein the Raman active particles have a size of 100 to 150 nm.

5. The digital surface-enhanced Raman scattering (SERS) sensing platform of claim 1, wherein the Raman reporter satisfies the following Chemical Formula 1:

$NO_2$—Ar—SH (Chemical Formula 1):

wherein Ar is (C6-C12) arylene group.

6. The digital surface-enhanced Raman scattering (SERS) sensing platform of claim 1, wherein the substance to be detected is a virus including SARS-COV-2 and a variant thereof.

7. The digital surface-enhanced Raman scattering (SERS) sensing platform of claim 1, wherein the excitation light is a near-infrared ray in a wavelength band of 750 to 800 nm.

8. The digital surface-enhanced Raman scattering (SERS) sensing platform of claim 1, wherein a relative standard deviation (% RSD) of a quantitative detection signal for the substance to be detected at an extremely low concentration in a range of 1 fM to 80 fM is 20% or less, the relative standard deviation of the quantitative detection signal for the substance to be detected being an indicator showing sensing reliability of the substance to be detected using the digital SERS sensing platform.

9. A detection method of a substance to be detected in a sample, the method comprising:

a) preparing a Raman probe in which a first receptor (detection antibody) which specifically binds to a substance to be detected is positioned on a surface of a Raman active particle including a spherical plasmonic metal core, a plasmonic metal shell having surface unevenness, and a self-assembled monolayer including a Raman reporter positioned between the core and the shell;

b) preparing a substrate having a second receptor (capture antibody) which specifically binds to the substance to be detected on the surface;

c) forming an analysis structure by bringing a sample including the substance to be detected into contact with the substrate of b) to capture the substance, and then further bringing the sample into contact with the Raman probe of a) to cap the substance;

d) detecting Raman spectroscopy by performing Raman mapping based on a Raman spectrum detected by irradiating the analysis structure with an excitation light; and e) obtaining a digital signal which is quantitatively detected by a combination of a Raman signal intensity calculated from the Raman spectrum and a digital count calculated from the Raman mapping;

wherein the digital count of e) is a total number of pixels of which the Raman signal intensity in the Raman map obtained by the Raman mapping performed in a predetermined area is more than a background threshold, wherein the background threshold is set using a sum of maximum Raman intensities obtained by Raman analysis performed for a reagent which does not include the Raman active particles and a background standard deviation, which is a standard deviation of the Raman intensity detected in each pixel, and wherein the digital signal is a product of the Raman signal intensity and the digital count.

10. The detection method of claim 9, wherein the excitation light irradiated in d) is a near-infrared ray in a wavelength band of 750 to 800 nm.

11. The detection method of claim 9, wherein a relative standard deviation (% RSD) of a digital signal for the substance to be detected at an extremely low concentration in a range of 1 fM to 80 fM is 20% or less, the relative standard deviation of the obtained digital signal being an indicator showing detection reliability of the substance to be detected.

12. The detection method of claim 9, wherein a limit of detection (LOD) of the substance to be detected by the detection method is 1 fM or less.

* * * * *